(12) United States Patent
Tsubuku et al.

(10) Patent No.: US 11,534,197 B2
(45) Date of Patent: Dec. 27, 2022

(54) ENERGY CONTROL DEVICE, TREATMENT SYSTEM, AND ACTUATING METHOD OF ENERGY CONTROL DEVICE

(71) Applicant: OLYMPUS CORPORATION, Hachioji (JP)

(72) Inventors: Yoshihiro Tsubuku, Fuchu (JP); Minoru Kawasaki, Tokyo (JP); Gen Kato, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 1008 days.

(21) Appl. No.: 16/257,483

(22) Filed: Jan. 25, 2019

(65) Prior Publication Data

US 2019/0150974 A1    May 23, 2019

Related U.S. Application Data

(63) Continuation of application No. PCT/JP2016/071867, filed on Jul. 26, 2016.

(51) Int. Cl.
*A61B 18/00* (2006.01)
*A61B 18/14* (2006.01)
(Continued)

(52) U.S. Cl.
CPC ...... *A61B 17/320092* (2013.01); *A61B 90/08* (2016.02); *A61B 18/1445* (2013.01);
(Continued)

(58) Field of Classification Search
CPC ........... A61B 17/320092; A61B 90/08; A61B 2018/00702; A61B 2090/0807
See application file for complete search history.

(56) References Cited

U.S. PATENT DOCUMENTS

2002/0161385 A1* 10/2002 Wiener .......... A61B 17/320068
606/169
2008/0255642 A1* 10/2008 Zarins .................... A61F 7/007
607/99
(Continued)

FOREIGN PATENT DOCUMENTS

JP    2009-254818 A    11/2009
JP      4579324 B2    11/2010
(Continued)

OTHER PUBLICATIONS

Nov. 12, 2019 Office Action issued in Japanese Patent Application No. 2018-530234.
(Continued)

*Primary Examiner* — Daniel W Fowler
*Assistant Examiner* — Annie L Patton
(74) *Attorney, Agent, or Firm* — Oliff PLC

(57) ABSTRACT

In an energy control device, a processor detects a gradual decrease start time at which the electric characteristic value in relation to electric energy output to an ultrasonic transducer starts a gradual decrease after a gradual increase. The processor calculates a difference value by subtracting the electric characteristic value from a peak value at gradual decrease start time and calculates an integrated value of the difference value from the gradual decrease start time. The processor executes, based on a fact that the integrated value become greater than a predetermined threshold, at least one of causing to stop or reduce the output of the electric energy to the ultrasonic transducer, and notifying that the integrated value become greater than the predetermined threshold.

9 Claims, 8 Drawing Sheets

(51) Int. Cl.
  *A61B 17/00* (2006.01)
  *A61B 90/00* (2016.01)
  *A61B 17/32* (2006.01)

(52) U.S. Cl.
  CPC ............... *A61B 2017/0003* (2013.01); *A61B 2017/00017* (2013.01); *A61B 2018/00589* (2013.01); *A61B 2018/00607* (2013.01); *A61B 2018/00666* (2013.01); *A61B 2018/00702* (2013.01); *A61B 2018/00779* (2013.01); *A61B 2018/00827* (2013.01); *A61B 2018/00875* (2013.01); *A61B 2018/00892* (2013.01); *A61B 2018/00994* (2013.01); *A61B 2090/0807* (2016.02)

(56) References Cited

U.S. PATENT DOCUMENTS

| | | |
|---|---|---|
| 2009/0259221 A1 | 10/2009 | Tahara et al. |
| 2009/0326569 A1 | 12/2009 | Tanaka et al. |
| 2010/0004669 A1 | 1/2010 | Smith et al. |
| 2011/0044635 A1 | 2/2011 | Ando et al. |
| 2011/0144635 A1* | 6/2011 | Harper ............... A61B 18/1206 606/34 |
| 2012/0310264 A1* | 12/2012 | Messerly ............... B06B 1/0284 606/169 |
| 2014/0324041 A1* | 10/2014 | Bowers ............... A61B 18/1206 606/40 |
| 2015/0258352 A1 | 9/2015 | Lin et al. |

FOREIGN PATENT DOCUMENTS

| | | |
|---|---|---|
| JP | 4649545 B2 | 3/2011 |
| JP | 5259883 B2 | 8/2013 |
| JP | 5851664 B1 | 2/2016 |
| JP | 5905172 B2 | 4/2016 |
| JP | 5911650 B2 | 4/2016 |
| JP | 5942045 B2 | 6/2016 |

OTHER PUBLICATIONS

Sep. 27, 2016 International Search Report issued International Patent Application No. PCT/JP2016/071867.
Sep. 27, 2016 International Search Report issued in International Patent Application No. PCT/JP2016/071866.
Nov. 12, 2019 Office Action issued in Japanese Patent Application No. 2018-530233.
Apr. 28, 2022 Office Action issued in U.S. Appl. No. 16/258,045.
U.S. Appl. No. 16/258,045, filed in the name of Yoshihiro Tsubuku et al., dated Jan. 25, 2019.

* cited by examiner

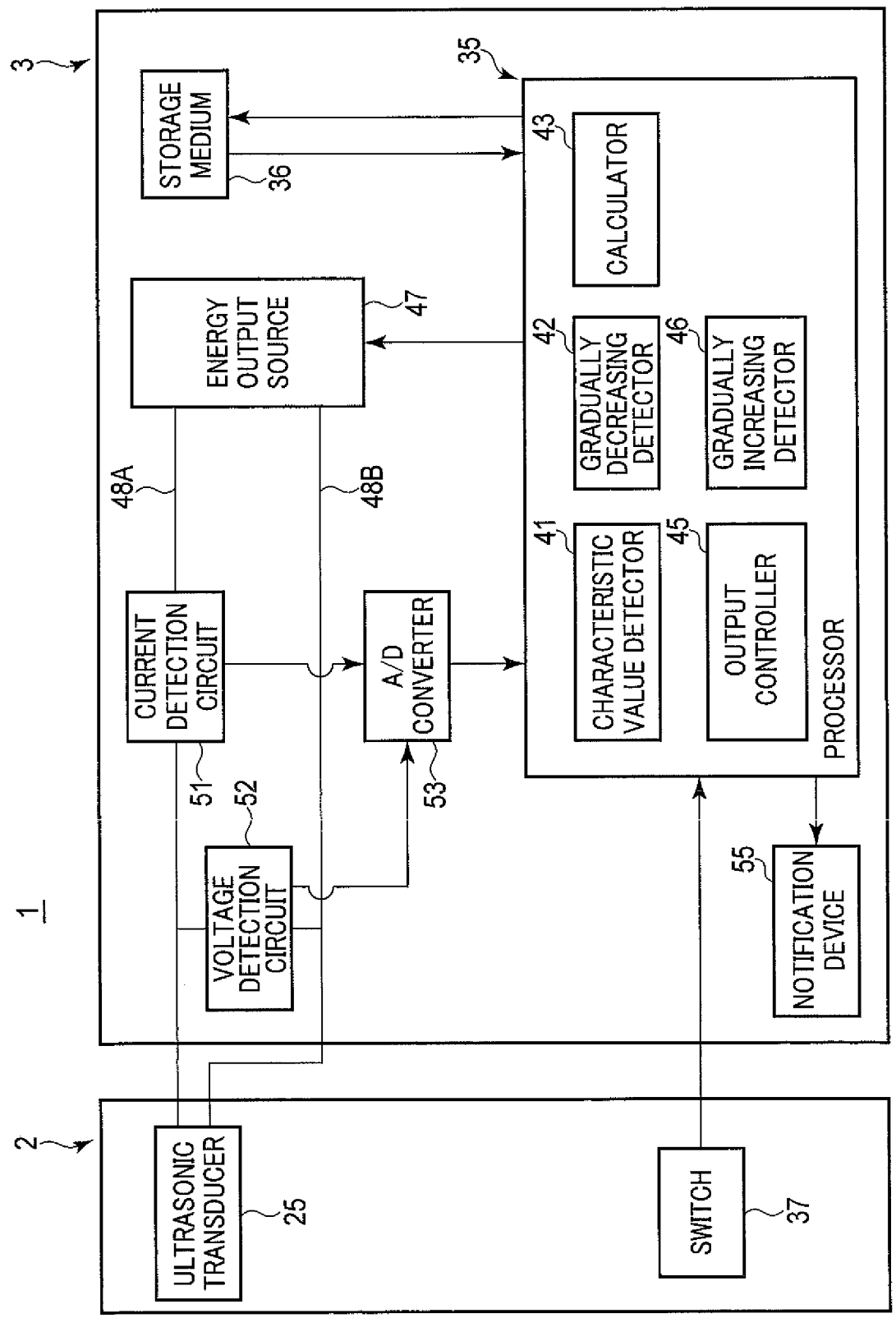
F I G. 2

US 11,534,197 B2

ENERGY CONTROL DEVICE, TREATMENT SYSTEM, AND ACTUATING METHOD OF ENERGY CONTROL DEVICE

CROSS-REFERENCE TO RELATED APPLICATIONS

This is a Continuation Application of PCT Application No. PCT/JP2016/071867, filed Jul. 26, 2016, the entire contents of which are incorporated herein by reference.

BACKGROUND OF THE INVENTION

1. Field of the Invention

The present invention relates to an energy control device for use in combination with an ultrasonic treatment instrument, and relates to a treatment system including the energy control device. Further, the present invention relates to an actuating method of the energy control device.

2. Description of the Related Art

U.S. Patent Application Publication No. 2012/0310264 discloses an ultrasonic treatment instrument in which a first grasping piece and a second grasping piece are provided in an end effector, the first and second grasping pieces being openable and closable relative to each other. In a treatment system including this ultrasonic treatment instrument, electric energy is supplied from an energy control device to an ultrasonic transducer of the ultrasonic treatment instrument, and thereby ultrasonic vibration is generated by the ultrasonic transducer. Then, the generated ultrasonic vibration is transmitted to the first grasping piece. In the state in which a treated target is grasped between the paired grasping pieces, the ultrasonic vibration is transmitted to the first grasping piece, and thereby frictional heat occurs between the first grasping piece and the treated target. By the frictional heat, the treated target is cut and opened, and, at the same time, coagulated.

BRIEF SUMMARY OF THE INVENTION

According to one aspect of the invention, an energy control device for use in combination with an ultrasonic treatment instrument, the ultrasonic treatment instrument including an ultrasonic transducer configured to generate ultrasonic vibration by being supplied with electric energy, and an end effector configured to perform a treatment by using the ultrasonic vibration generated by the ultrasonic transducer, the energy control device including: an energy output source configured to output the electric energy to the ultrasonic transducer; and a processor configured to: detect an electric characteristic value in relation to the electric energy which is output to the ultrasonic transducer; detect, based on a detection result of the electric characteristic value, a gradual decrease start time at which the electric characteristic value starts a gradual decrease after the electric characteristic value gradually increases; calculate, with the electric characteristic value at the gradual decrease start time being set as a peak value, an integrated value of a difference value from the gradual decrease start time, the difference value being obtained by subtracting the electric characteristic value from the peak value; and execute, based on a fact that the integrated value become greater than a predetermined threshold after the gradual decrease start time, at least one of causing the energy output source to stop or reduce the output of the electric energy to the ultrasonic transducer, and notifying that the integrated value become greater than the predetermined threshold.

According to one another aspect of the invention, an actuating method of an energy control device, the energy control device being used in combination with an ultrasonic treatment instrument, the ultrasonic treatment instrument including an ultrasonic transducer configured to generate ultrasonic vibration by being supplied with electric energy, and an end effector configured to perform a treatment by using the ultrasonic vibration generated by the ultrasonic transducer, the actuating method including: outputting the electric energy to the ultrasonic transducer; detecting an electric characteristic value in relation to the electric energy which is output to the ultrasonic transducer; detecting, based on a detection result of the electric characteristic value, a gradual decrease start time at which the electric characteristic value starts a gradual decrease after the electric characteristic value gradually increases; calculating, with the electric characteristic value at the gradual decrease start time being set as a peak value, an integrated value of a difference value from the gradual decrease start time, the difference value being obtained by subtracting the electric characteristic value from the peak value; and executing, based on a fact that the integrated value become greater than a predetermined threshold after the gradual decrease start time, at least one of stopping or reducing the output of the electric energy to the ultrasonic transducer, and notifying that the integrated value become greater than the predetermined threshold.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a block diagram illustrating a configuration relating to the supply of electric energy from an energy control device according to the first embodiment to an ultrasonic treatment instrument;

DETAILED DESCRIPTION OF THE INVENTION

First Embodiment

Figure 1:
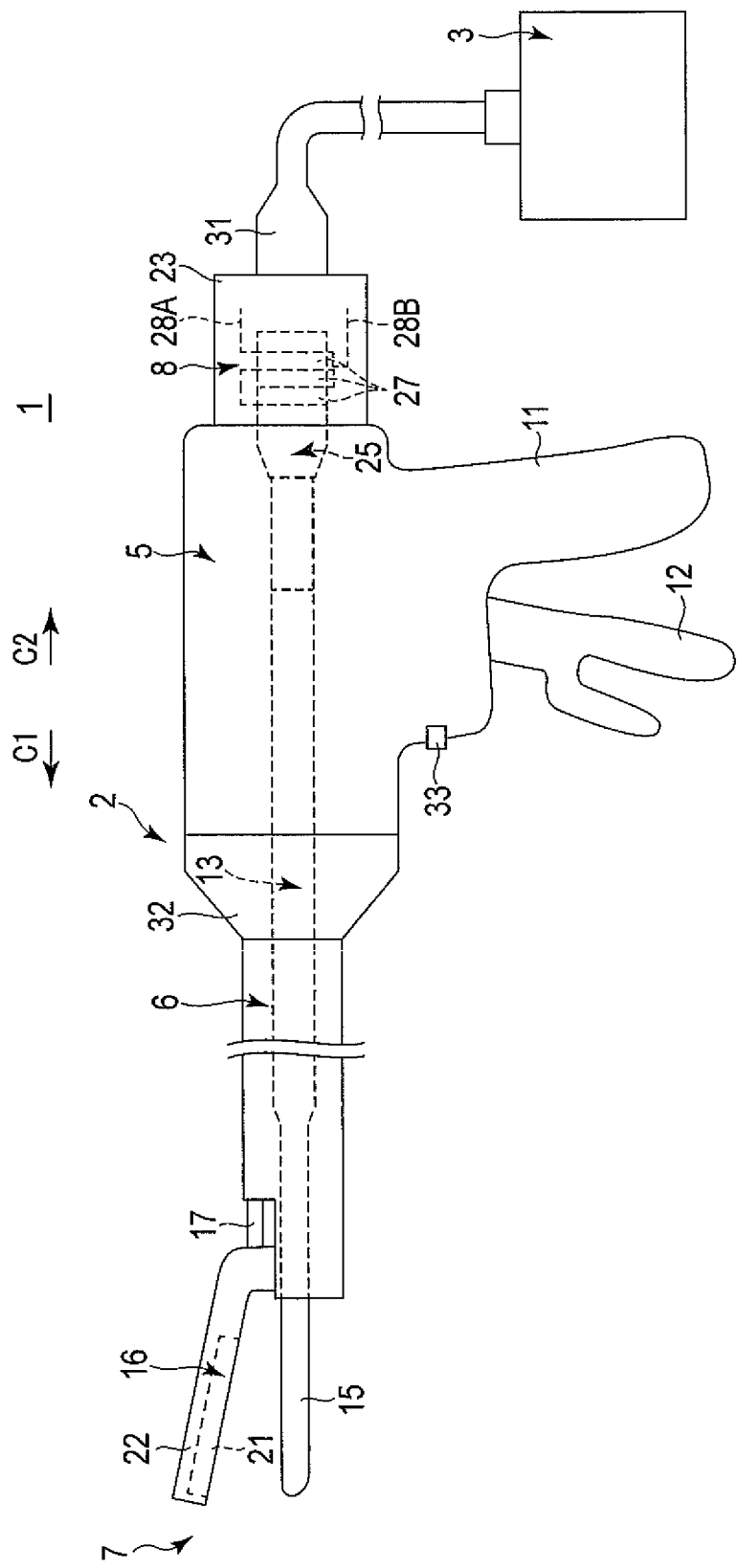
FIG. 1 is a schematic view illustrating a treatment system according to a first embodiment.

A first embodiment of the present invention will be described with reference to FIG. 1 to FIG. 5. FIG. 1 is a view illustrating a treatment system 1. As illustrated in FIG. 1, the treatment system 1 includes an ultrasonic treatment instrument 2 and an energy control device 3. Here, in FIG. 1, an arrow C1 side is defined as a distal side, and an arrow C2 side is defined as a proximal side. The proximal side is opposite to the distal side.

The ultrasonic treatment instrument 2 includes a housing 5 which can be held, a shaft (sheath) 6 coupled to the distal side of the housing 5, an end effector 7 provided in a distal portion of the shaft 6, and a transducer unit 8 coupled to the housing 5 from the proximal side. The housing 5 is provided with a grip 11, and a handle 12 is rotatably attached to the housing 5. By the handle 12 rotating relative to the housing 5, the handle 12 opens or closes relative to the grip 11.

In the ultrasonic treatment instrument 2, a rod member (probe) 13 extends toward the distal side from the inside of the housing 5 through the inside of the shaft 6. The rod member 13 is formed of a material with a high vibration transmissibility such as 64 titanium (Ti-6Al-4V). A distal portion of the rod member 13 is provided with a first grasping piece (treatment section) 15. The rod member 13 is inserted through the shaft 6 in the state in which the first grasping piece 15 projects toward the distal side from the distal end of the shaft 6.

In addition, a second grasping piece (jaw) 16 is rotatably attached to the distal portion of the shaft 6. A movable member 17 extends in the inside of the shaft 6 from the proximal side toward the distal side. A distal portion of the movable member 17 is connected to the second grasping piece 16, and a proximal portion of the movable member 17 is coupled to the handle 12 in the inside of the housing 5. By opening or closing the handle 12 relative to the grip 11, the movable member 17 moves toward the proximal side or distal side. Thereby, the second grasping piece 16 rotates relative to the shaft 6, and the second grasping piece 16 opens or closes relative to the first grasping piece 15. In other words, the paired grasping pieces 15 and 16 can open and close relative to each other.

In the present embodiment, the end effector 7 is formed by the paired grasping pieces 15 and 16. The second grasping piece 16 includes a pad member 21, and a holder member 22 to which the pad member 21 is attached. The pad member 21 is formed of a resin such as PTFE (polytetrafluoroethylene). In the state in which the grasping pieces 15 and 16 are closed, the pad member 21 is abuttable on the first grasping piece 15. In the state in which the pad member 21 abuts on the first grasping piece 15, a part other than the pad member 21 in the second grasping piece 16, for instance, the holder member 22, does not come in contact with the first grasping piece 15.

The transducer unit 8 includes a transducer case 23, and an ultrasonic transducer 25 provided in the inside of the transducer case 23. In the inside of the housing 5, the ultrasonic transducer 25 is connected to the rod member 13 from the proximal side. The ultrasonic transducer 25 includes at least one piezoelectric element 27, and electrodes 28A and 28B. Each of the piezoelectric elements 27 is interposed between the electrodes 28A and 28B. One end of a cable 31 is connected to the transducer case 23. The other end of the cable 31 is detachably connected to the energy control device 3. In the meantime, in one example, the transducer case 23 is not provided, and the ultrasonic transducer 25 is disposed in the inside of the housing 5. In this case, the one end of the cable 31 is connected to the housing 5.

In addition, in the present embodiment, a rotation member (rotation knob) 32 is attached to the housing 5. By rotating the rotation member 32, the shaft 6, the rod member 13 including the first grasping piece 15, the second grasping piece 16, and the ultrasonic transducer 25 rotate, together with the rotation member 32, relative to the housing 5 around the center axis of the shaft 6. Thereby, the angular position of the end effector 7 around the center axis of the shaft 6 is adjusted. In one example, the rotation member 32 may not be provided.

In addition, an operation button 33 is attached to the housing 5. An operation for supplying electric energy from the energy control device 3 to the ultrasonic transducer 25 is input by the operation button 33. In one example, a footswitch, which is separate from the ultrasonic treatment instrument 2, may be provided in place of the operation button 33, or in addition to the operation button 33.

FIG. 2 is a view illustrating a configuration relating to the supply of electric energy from the energy control device 3 to the ultrasonic treatment instrument 2. As illustrated in FIG. 2, the energy control device 3 includes a processor 35 which controls the entirety of the treatment system 1, and a storage medium 36. The processor (controller) is composed of an integrated circuit including a CPU (Central Processing Unit), ASIC (Application Specific Integrated Circuit), FPGA (Field Programmable Gate Array) or the like. The processor 35 may be composed of a single integrated circuit or a plurality of integrated circuits. In addition, in the energy control device 3, one processor 35 may be provided, or a plurality of processors 35 may be provided separately. A process in the processor 35 is executed according to a program stored in the processor 35 or in the storage medium 36. Further, the storage medium 36 stores a processing program which is used in the processor 35, and parameters, tables, etc. which are used in arithmetic calculations in the processor 35. The processor 35 includes a characteristic value detector 41, a gradually decreasing detector 42, a calculator 43, an output controller 45, and a gradually increasing detector 46. The characteristic value detector 41, gradually decreasing detector 42, calculator 43, output controller 45 and gradually increasing detector 46 function as parts of the processor 35 and perform parts of the process which is executed by the processor 35.

A switch 37 is provided in the inside of the housing 5 of the ultrasonic treatment instrument 2. The switch 37 is changed over from an OFF state to an ON state by an operation input being performed by the operation button 33.

Based on the change-over of the switch 37 to the ON state, the processor 35 detects that the operation was input by the operation button 33.

The energy control device 3 includes an energy output source 47. The energy output source 47 is electrically connected to the ultrasonic transducer 25 via electric paths 48A and 48B. Here, the electric path 48A extends through the inside of the cable 31 and electrically connects the energy output source 47 and the electrode 28A. In addition, the electric path 48B extends through the inside of the cable 31 and electrically connects the energy output source 47 and the electrode 28B. The energy output source 47 includes a conversion circuit or the like, which converts electric power from a battery power source or a plug socket power source to electric energy which is supplied to the ultrasonic transducer 25. The energy output source 47 outputs the electric energy converted by the conversion circuit. Further, the electric energy that is output from the energy output source 47 is supplied to the ultrasonic transducer 25 via the electric paths 48A and 48B. The output controller 45 of the processor 35 controls the output of electric energy from the energy output source 47. Note that AC electric power with a certain frequency in a predetermined frequency range is output as electric energy from the energy output source 47.

By the supply of electric energy to the ultrasonic transducer 25, a voltage is applied between the electrodes 28A and 28B, and AC electric current flows in each of the piezoelectric elements 27. Thereby, the AC electric current is converted to ultrasonic vibration by the piezoelectric elements 27, and ultrasonic vibration is generated by the ultrasonic transducer 25. The generated ultrasonic vibration is transmitted from the proximal side toward the distal side through the rod member 13. Then, the ultrasonic vibration is transmitted to the first grasping piece 15, and the rod member 13 including the first grasping piece 15 vibrates. At this time, the rod member 13 vibrates substantially in parallel to the longitudinal direction of the rod member 13 at a certain frequency (e.g. 47 kHz) in a predetermined frequency range (e.g. a range between 46 kHz and 48 kHz). The end effector 7 performs a treatment by using the ultrasonic vibration which is transmitted to the first grasping piece 15.

The energy control device 3 includes a current detection circuit 51 and a voltage detection circuit 52. The current detection circuit 51 detects a current value of an output current I from the energy output source 47 to the ultrasonic transducer 25, and the voltage detection circuit 52 detects a voltage value of an output voltage V from the energy output source 47 to the ultrasonic transducer 25. In addition, the energy control device 3 is provided with an A/D converter 53. An analog signal indicative of the current value detected by the current detection circuit 51 and an analog signal indicative of the voltage value detected by the voltage detection circuit 52 are sent to the A/D converter 53. The A/D converter 53 converts the analog signal indicative of the current value and the analog signal indicative of the voltage value to digital signals, and sends the converted digital signals to the processor 35.

The characteristic value detector 41 of the processor 35 detects an impedance Z of the ultrasonic transducer 25, based on the detection result of the output current I by the current detection circuit 51 and the detection result of the output voltage V by the voltage detection circuit 52. Specifically, the characteristic value detector 41 detects the impedance Z of the ultrasonic transducer 25 as an electric characteristic value in relation to the electric energy which is output to the ultrasonic transducer 25.

In the present embodiment, in the state in which the electric energy is being supplied from the energy output source 47 to the ultrasonic transducer 25, the output controller 45 of the processor 35 controls the output of electric energy from the energy output source 47 by constant current control which keeps the current value of the output current I constant with time. In this case, the output voltage V from the energy output source 47 is adjusted in accordance with the variation of the impedance Z. Specifically, when the impedance Z increases, the output voltage V is increased and the current value of the output current I is kept constant with time. In this case, output electric power P also increases in accordance with the increase of the output voltage V. Conversely, when the impedance Z decreases, the output voltage V is decreased and the current value of the output current I is kept constant with time. In this case, the output electric power P also decreases in accordance with the decrease of the output voltage V.

In the present embodiment, the gradually decreasing detector 42 of the processor 35 detects a gradual decrease start time at which the impedance Z starts a gradual decrease after a gradual increase, based on the detection result by the characteristic value detector 41. In addition, the gradually increasing detector 46 detects a gradual increase start time at which the impedance Z starts a gradual increase, based on the detection result by the characteristic value detector 41. Besides, the calculator 43 performs an arithmetic calculation, for example, based on the detection result by the characteristic value detector 41. Based on the detection results by the characteristic value detector 41, gradually decreasing detector 42 and gradually increasing detector 46, and based on the calculation result by the calculator 43, the output controller 45 executes judgment, and controls the output of electric energy from the energy output source 47.

In one example, a notification device 55 may be provided in the energy control device 3, or separately from the energy control device 3. In this case, the processor 35 controls the actuation of the notification device 55, based on the detection results by the characteristic value detector 41, gradually decreasing detector 42 and gradually increasing detector 46, and based on the calculation result by the calculator 43. The notification device 55 performs notification by any one of buzzer sound, turn-on of light, screen display, etc.

Next, the function and advantageous effects of the energy control device 3 and treatment system 1 of the present embodiment will be described. When a treated target, such as a biological tissue, is treated by using the treatment system 1, a surgeon holds the housing 5 and inserts the end effector 7 into a body cavity such as the abdominal cavity. Then, the treated target, such as a biological tissue, is disposed between the grasping pieces 15 and 16, and the handle 12 is closed relative to the grip 11. Thereby, the second grasping piece 16 closes relative to the first grasping piece 15, and the treated target is grasped between the grasping pieces 15 and 16. In this state, the surgeon performs an operation input by the operation button 33. Thereby, the switch 37 is set in the ON state, and the processor 35 detects that the operation input was performed by the operation button 33.

By the detection of the operation input by the operation button 33, the output controller 45 of the processor 35 causes the energy output source 47 to output electric energy to the ultrasonic transducer 25. Thereby, ultrasonic vibration is generated by the ultrasonic transducer 25, and the generated ultrasonic vibration is transmitted to the first grasping piece 15 through the rod member 13. By the ultrasonic vibration being transmitted to the first grasping piece (probe treatment section) 15 in the state in which the treated target is grasped between the grasping pieces 15 and 16, frictional heat occurs between the first grasping piece 15 and the grasped treated target. By the frictional heat, the treated target is cut and opened and, at the same time, coagulated.

A process, which is executed by the processor 35, is described. Here, time t is defined. In addition, the impedance Z of the ultrasonic transducer 25 at time t is indicated as Z(t). Besides, in the present embodiment, the processor 35 sets an impedance maximum value Zmax as a judgment parameter. The impedance maximum value Zmax is a maximum value of the impedance Z from a certain time point defined by a condition to a time point at which the impedance Z(t) occurs. The impedance maximum value Zmax is set, for example, based on a variation with time of the impedance Z. In the state in which the impedance Z is gradually decreasing, the impedance Z(t) at the gradual decrease start time is the impedance maximum value Zmax, and the impedance maximum value Zmax is the peak value of the impedance Z(t). In addition, in the state in which the impedance Z is gradually decreasing, the calculator 43 calculates a difference value (Zmax−Z(t)) which is obtained by subtracting the impedance Z(t) from the peak value of the impedance Z(t) at the gradual decrease start time, which is the impedance maximum value Zmax, and calculates an integrated value Σ(Zmax−Z(t)) of the difference value (Zmax−Z(t)) from the gradual decrease start time to a time point of the occurrence of the impedance Z(t).

In the present embodiment, the output of electric energy is controlled, based on the impedance Z of the ultrasonic transducer 25, which is the electric characteristic value of the electric energy that is output from the energy output source 47. In addition, the output of electric energy is controlled, based on the above-described integrated value Σ(Zmax−Z(t)) of the difference value (Zmax−Z(t)) from the gradual decrease start time. Here, the impedance Z of the ultrasonic transducer 25 varies in accordance with a load on the ultrasonic transducer 25 and a load on the rod member 13 which is connected to the ultrasonic transducer 25.

Figure 3:
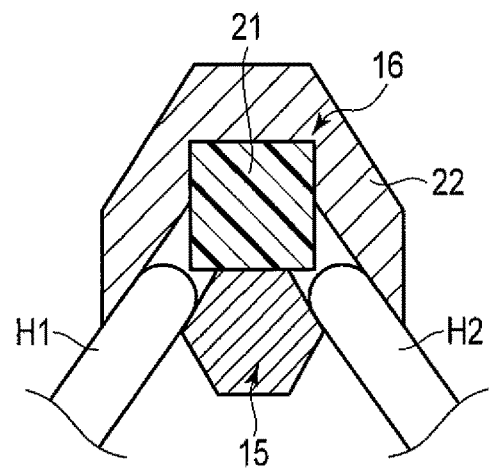
FIG. 3 is a cross-sectional view schematically illustrating a part in which a treated target grasped by an end effector according to the first embodiment is divided by cutting, by a cross section substantially perpendicular to a longitudinal direction of the end effector.

In addition, in a treatment using the treatment system 1, the treated target grasped between the paired grasping pieces 15 and 16 is cut and opened, while being coagulated, as described above. Thereby, the range of the treated target, which is grasped between the grasping pieces 15 and 16, is divided in a width direction of the end effector 7. The phenomenon, in which the treated target is divided in the width direction of the end effector 7, is referred to as "division by cutting". FIG. 3 illustrates a part, in which the treated target was divided by cutting, by a cross section substantially perpendicular to the longitudinal direction of the end effector 7. As illustrated in FIG. 3, in the part in which the treated target was divided by cutting, the treated target is divided into a one-side region H1 in the width direction of the end effector 7 and an other-side region H2 in the width direction of the end effector 7. In addition, the pad member 21 of the second grasping piece 16 comes in contact with the first grasping piece 15 between the mutually divided regions H1 and H2.

In the state in which the treated target is cut and opened, while being coagulated, by the ultrasonic vibration, the pushing force from the second grasping piece 16 toward the first grasping piece 15 gradually decreases until division by cutting occurs in a part of the range of the treated target grasped between the grasping pieces 15 and 16, because the opening angle between the grasping pieces 15 and 16 decreases due to the cutting and opening of the treated target and because the state of the treated target varies. Thus, the load on the rod member 13 gradually decreases. Accordingly, the impedance Z of the ultrasonic transducer 25 gradually decreases until the division by cutting occurs in a part of the grasped range of the treated target and the resin-made pad member 21 comes in contact with the first grasping piece 15. Here, the "gradually decreasing" means that the impedance Z gradually decreases with the passing of time t, and includes a state in which the impedance Z gradually decreases with the inclusion of a small increase and decrease of several-ten Ω or less.

If division by cutting occurs in a part of the grasped range of the treated target, the resin-made pad member 21 comes in contact with the first grasping piece 15 in the part in which the treated target was divided by cutting, as described above. If a part of the pad member 21 begins to come in contact with the first grasping piece 15, the load on the rod member 13 gradually increases until the entirety of the grasped range of the treated target is divided by cutting and almost the entire length of the pad member 21 comes in contact with the first grasping piece 15. Accordingly after division by cutting occurred in a part of the grasped range of the treated target, the impedance Z gradually increases. Here, the "gradually increasing" means that the impedance Z gradually increases with the passing of time t, and includes a state in which the impedance Z gradually increases with the inclusion of a small increase and decrease of several-ten Ω or less.

In addition, if the most part or the entirety of the grasped range of the treated target is divided by cutting, the most part or substantially the entire length of the pad member 21 in the extending direction comes in contact with the first grasping piece 15. After substantially the entire length of the pad member 21 is put in contact with the first grasping piece 15, the opening angle between the grasping pieces 15 and 16 does not substantially change. In addition, if substantially the entire length of the pad member 21 is put in contact with the first grasping piece 15, a contact part between the pad member 21 and first grasping piece 15 begins to be abraded and dissolved by frictional heat due to ultrasonic vibration, and thus the load on the rod member 13 gradually decreases. Accordingly, after division by cutting occurred in the entirety of the grasped range of the treated target, the impedance Z gradually decreases.

Further, after a certain length of time has passed since the entirety of the grasped range of the treated target was divided by cutting, the state of the contact part between the pad member 21 and first grasping piece 15 is stabilized. Thus, a variation of the load on the rod member 13 decreases, and the variation of the impedance Z decreases. Since a certain length of time has passed since the impedance Z started the gradual decrease due to the vision by cutting, the impedance Z decreases by some degree from the gradual decrease start time. Thus, at a timing when a certain length of time has passed since the gradual decrease start time of the impedance Z, the above-described integrated value Σ(Zmax−Z(t)) of the difference value (Zmax−Z(t)) from the gradual decrease start time increases to some degree and becomes greater than a predetermined threshold ΣZth. In the meantime, if the rod member 13 is further vibrated by ultrasonic vibration after the variation of the impedance Z has decreased, the pad member 21 that is in contact with the first grasping piece 15 is deformed by frictional heat. By the deformation of the pad member 21, the load on the rod member 13 gradually increases, and the impedance Z gradually increases.

Figure 4:
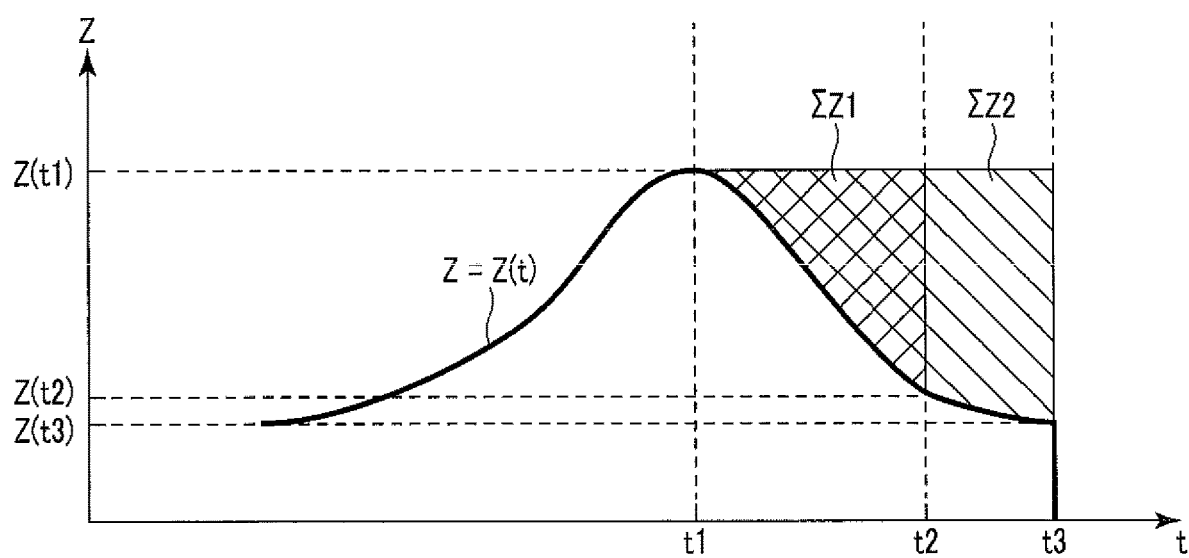
FIG. 4 is a schematic view illustrating an example of a variation with time of an impedance of the ultrasonic transducer in a state in which a grasped treated target is cut and opened, while being coagulated, by ultrasonic vibration.

FIG. 4 is a view illustrating an example of a variation with time of the impedance Z of the ultrasonic transducer 25 in the state in which the grasped treated target is cut and opened, while being coagulated, by ultrasonic vibration. In FIG. 4, the ordinate axis indicates the impedance Z, and the abscissa axis indicates time t. In the example illustrated in FIG. 4, the impedance Z gradually increases until time t1. Then, at time t1 after the gradual increase, the impedance Z begins to gradually decrease. Accordingly, the time t1 is a gradual decrease start time at which the impedance Z begins to gradually decrease after the gradual increase. In addition, in the example of FIG. 4, at or immediately near time t1, the entirety of the grasped range of the treated target is divided by cutting.

Besides, in the example of FIG. 4, time t2 after time t1, and time t3 after time t2 are defined. Further, the integrated value $\Sigma(Zmax-Z(t))$ from time t1 that is the gradual decrease start time to time t2 is defined as $\Sigma Z1$, and the integrated value $\Sigma(Zmax-Z(t))$ from time t1 to time t3 is defined as $\Sigma Z2$. In the example of FIG. 4, the integrated value $\Sigma Z1$ is not greater than the predetermined threshold $\Sigma Zth$, and the integrated value $\Sigma Z2$ is greater than the predetermined threshold $\Sigma Zth$. Besides, the integrated value $\Sigma(Zmax-Z(t))$ of the difference value $(Zmax-Z(t))$ from time t1 that is the gradual decrease start time changes, at time t3, from the state in which the integrated value $\Sigma(Zmax-Z(t))$ is not greater than the predetermined threshold $\Sigma Zth$ to the state in which the integrated value $\Sigma(Zmax-Z(t))$ is greater than the predetermined threshold $\Sigma Zth$. In addition, in the example of FIG. 4, at time t3, there occurs substantially no deformation of the pad member 21 due to frictional heat. Note that in the example of FIG. 4, an area of a part surrounded by a straight line t=t2, a straight line Z=Z(t1) and a curve lineZ=Z(t) becomes the integrated value $\Sigma Z1$ of the difference value $(Zmax-Z(t))$ from time t1 to time t2. An area of a part surrounded by a straight line t=t3, straight line Z=Z(t1) and curve line Z=Z(t) becomes the integrated value $\Sigma Z2$ of the difference value $(Zmax-Z(t))$ from time t1 to time t3.

Figure 5:
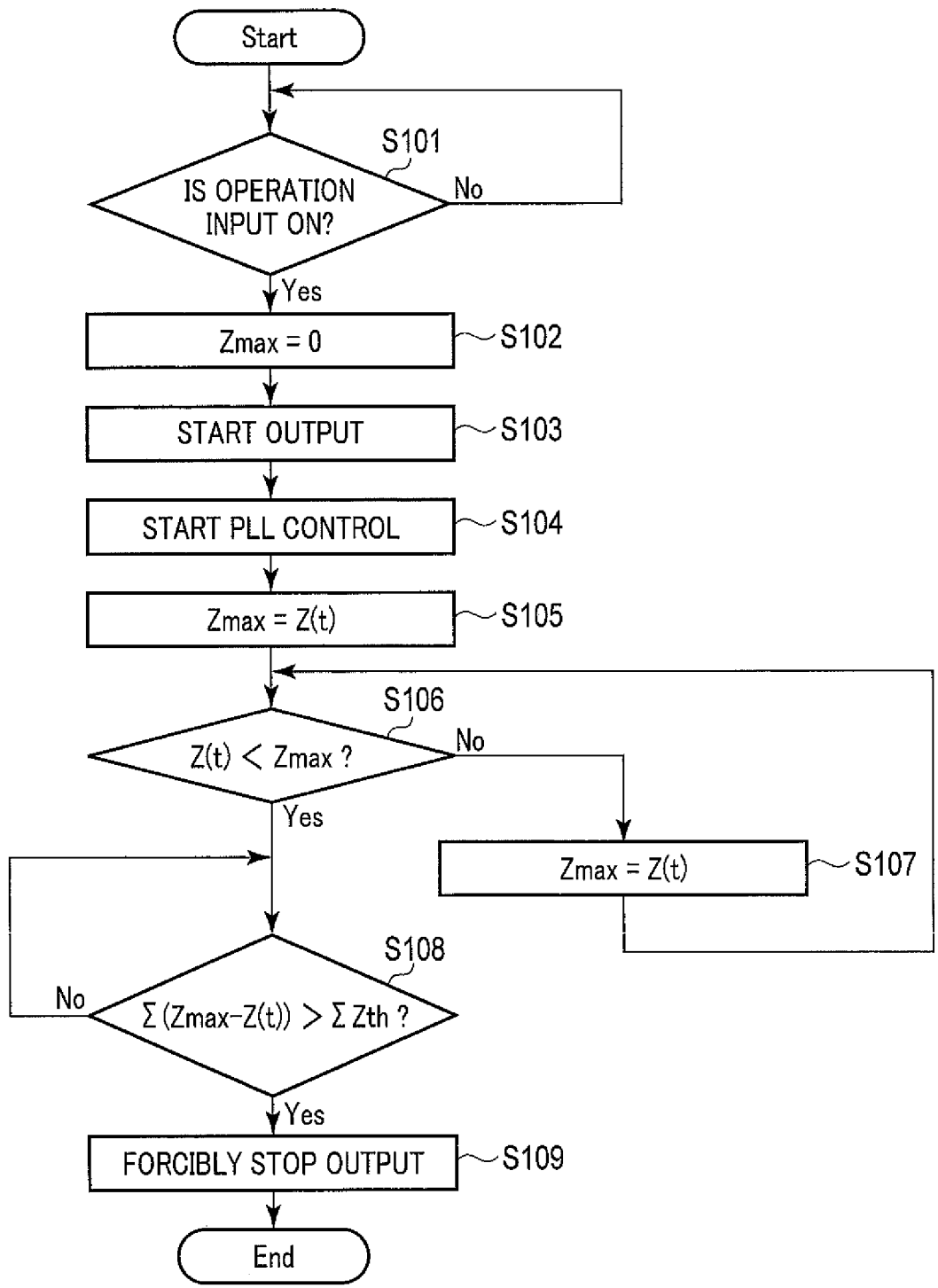
FIG. 5 is a flowchart illustrating a process in a processor of the energy control device according to the first embodiment.

FIG. 5 is a flowchart illustrating a process in the processor 35 of the energy control device 3, which is based on the operation input by the operation button 33. As illustrated in FIG. 5, the output controller 45 of the processor 35 judges whether the operation input was executed by the operation button 33, i.e. whether the operation input by the operation button 33 is ON or OFF, based on whether the switch 37 is in the ON state or not (step S101). When the operation input is not executed (step S101-No), the process returns to step S101. Specifically, the processor (controller) 35 stands by until the operation input is executed by the operation button 33.

If the operation input is executed (step S101—Yes), the processor 35 resets to zero the impedance maximum value Zmax which is a judgment parameter (step S102). Then, the output controller 45 of the processor 35 starts the output of electric energy from the energy output source 47 to the ultrasonic transducer 25 (step S103). After the start of the output of electric energy to the ultrasonic transducer 25, if a predetermined condition is satisfied, the output controller 45 of the processor 35 starts PLL (Phase Locked Loop) control with respect to the electric energy that is output from the energy output source 47 (step S104). By the PLL control, the frequency in the output of electric energy from the energy output source 47 is adjusted in such a state that the phase difference between the output current I and output voltage V becomes lower than a predetermined threshold value.

If the PLL control is started, the characteristic value detector 41 of the processor 35 starts detecting the impedance Z of the ultrasonic transducer 25 as the electric characteristic value of electric energy. In addition, at the time of the start of the PLL control or immediately after the start of the PLL control, the processor 35 sets the impedance maximum value Zmax at the impedance Z(t) (step S105). From the start time of the PLL control, the output controller 45 of the processor 35 controls the output of electric energy from the energy output source 47 by the above-described constant current control which keeps the current value of the output current I constant with time. Since the current value of the output current I is kept constant with time, the amplitude and vibration velocity of ultrasonic vibration generated by the ultrasonic transducer 25 also become substantially constant with time, and the amplitude and vibration velocity of ultrasonic vibration in the first grasping piece 15 become substantially constant with time.

Further, after the start time of the PLL control, the gradually decreasing detector 42 of the processor 35 judges, based on the detection result of the impedance Z by the characteristic value detector 41, whether the impedance Z(t) at time t is less than the impedance maximum value Zmax that is set (step S106). If the impedance Z(t) is not less than the impedance maximum value Zmax (step S106-No), the processor 35 updates the impedance maximum value Zmax to the impedance Z(t) at time t (step S107). Then, the process returns to step S106. Specifically, the processor 35 stands by until the impedance Z(t) becomes less than the impedance maximum value Zmax. On the other hand, if the impedance Z(t) is less than the impedance maximum value Zmax (step S106—Yes), the processor 35 holds, without updating, the impedance maximum value Zmax. Then, the process advances to step S108. By the execution of the process of steps S106 and S107, the gradually decreasing detector 42 of the processor 35 detects, as the gradual decrease start time at which the impedance Z starts a gradual decrease after a gradual increase, the time point when the state in which the impedance Z(t) is not less than the impedance maximum value Zmax changed to the state in which the impedance Z(t) is less than the impedance maximum value Zmax.

Then, the calculator 43 of the processor 35 calculates the difference value $(Zmax-Z(t))$ which is obtained by subtracting the impedance Z(t) from the peak value of the impedance Z(t) at the gradual decrease start time, which is the impedance maximum value Zmax, and calculates the integrated value $\Sigma(Zmax-Z(t))$ of the difference value $(Zmax-Z(t))$ from the gradual decrease start time. Further, the output controller 45 of the processor 35 judges whether the calculated integrated value $\Sigma(Zmax-Z(t))$ from the gradual decrease start time to time t is greater than a predetermined threshold $\Sigma Zth$ (step S108). Here, the predetermined threshold $\Sigma Zth$ is a positive value.

In the meantime, in one example, the energy control device 3 is provided with an input device (not shown) such as a touch panel, and a user interface (not shown), and the predetermined threshold $\Sigma Zth$ is set by the surgeon through the input device. In another example, the ultrasonic treatment instrument 2 is provided with a storage medium (not shown), and the predetermined threshold $\Sigma Zth$ is stored in the storage medium. In this case, by the ultrasonic treatment instrument 2 being connected to the energy control device 3 via the cable 31, the processor 35 reads the predetermined threshold $\Sigma Zth$ from the storage medium of the ultrasonic treatment instrument 2. In addition, the processor 35 automatically sets the predetermined threshold $\Sigma Zth$ which was read. Besides, the predetermined threshold $\Sigma Zth$ may be a preset fixed value. Alternatively, the predetermined threshold $\Sigma Zth$ may be set based on, e.g. a variation with time of the impedance Z. In one example, the storage medium 36 may store a lookup table or the like, which indicates the relationship between the predetermined threshold $\Sigma Zth$ and the kind of the ultrasonic treatment instrument 2. In this case, identification information, such as a serial number, is stored in the storage medium (not shown) of the ultrasonic treatment instrument 2, and the processor 35 reads the identification information from the storage medium of the ultrasonic treatment instrument 2, by the ultrasonic treatment instrument 2 being connected to the energy control device 3 via the cable 31. Then, based on the read identification information, the processor 35 detects the kind of the ultrasonic treatment instrument 2 which is connected to the energy control device 3. In addition, the processor 35 reads, from the lookup table, the predetermined threshold $\Sigma Z\text{th}$ which corresponds to the detected kind of the ultrasonic treatment instrument 2, and sets the predetermined threshold $\Sigma Z\text{th}$ to the read value.

When it is judged that the integrated value $\Sigma(Z\text{max}-Z(t))$ is greater than the predetermined threshold $\Sigma Z\text{th}$ (step S108—Yes), the output controller 45 of the processor 35 forcibly stops the output of electric energy from the energy output source 47 to the ultrasonic transducer 25 (step S109). On the other hand, when it is judged that the integrated value $\Sigma(Z\text{max}-Z(t))$ is not greater than the predetermined threshold $\Sigma Z\text{th}$ (step S108—No), the process returns to step S108. Then, the processor 35 stands by until the integrated value $\Sigma(Z\text{max}-Z(t))$ exceeds the predetermined threshold $\Sigma Z\text{th}$.

In one example, instead of stopping the output from the energy output source 47 in step S109, the output controller 45 may make the output of electric energy from the energy output source 47 lower than before the time point when it was judged that the integrated value $\Sigma(Z\text{max}-Z(t))$ is greater than the predetermined threshold $\Sigma Z\text{th}$. In this case, the output controller 45 makes the current value of the output current I from the energy output source 47 lower than before the time point when it was judged that the integrated value $\Sigma(Z\text{max}-Z(t))$ is greater than the predetermined threshold $\Sigma Z\text{th}$. Thereby, the amplitude and vibration velocity of ultrasonic vibration generated by the ultrasonic transducer 25 become lower, and the amplitude and vibration velocity of ultrasonic vibration in the first grasping piece 15 become lower, than before the time point when it was judged that the integrated value $\Sigma(Z\text{max}-Z(t))$ is greater than the predetermined threshold $\Sigma Z\text{th}$. Since the amplitude and vibration velocity of ultrasonic vibration in the first grasping piece 15 become lower, the performance of cutting and opening the grasped treated target by the ultrasonic vibration become lower.

In another example, in step S109, instead of stopping or reducing the output of electric energy from the energy output source 47, or in addition to stopping or reducing the output of the electric energy, the processor 35 may activate the notification device 55. Thereby, the notification device 55 notifies that the integrated value $\Sigma(Z\text{max}-Z(t))$ of the difference value $(Z\text{max}-Z(t))$ from the gradual decrease start time has become greater than the predetermined threshold $\Sigma Z\text{th}$. When only the notification by the notification device 55 is performed, the surgeon releases, based on the notification by the notification device 55, the operation input by the operation button 33, and stops the output of electric energy from the energy output source 47 to the ultrasonic transducer 25.

In the present embodiment, the process illustrated in FIG. 5 is executed as described above. Thus, if the impedance Z varies with time, as illustrated in FIG. 4, the impedance maximum value Zmax is set at the impedance Z(t) by the process of step S105 at or immediately after the start time of the PLL control. In addition, until time t1, by the process of steps S106 and S107, the impedance maximum value Zmax is continuously updated to the impedance Z(t). Thus, until time t1, the process does not advance to step S108. Accordingly, until time t1, the process of step S108 of judging whether the integrated value $\Sigma(Z\text{max}-Z(t))$ is greater than the predetermined threshold $\Sigma Z\text{th}$ is not executed.

Further, immediately after time t1, the gradually decreasing detector 42 judges, by the process of step S106, that the impedance Z(t) is not greater than the impedance Z(t1) that is the impedance maximum value Zmax. Thereby, the gradually decreasing detector 42 detects the time t1 as the gradual decrease start time of the impedance Z, and detects the impedance Z(t) at time t1, which is the gradual decrease start time, as the peak value of the impedance Z(t). From time t1, the impedance Z continuously gradually decreases. Thus, from time t1, the impedance Z(t1) at time t1 is held as the impedance maximum value Zmax.

From time t1, the calculator 43 calculates the difference value $(Z\text{max}-Z(t))$ which is obtained by subtracting the impedance Z(t) from the impedance Z(t1) at time t1 which is held as the impedance maximum value Zmax, and calculates the integrated value $\Sigma(Z\text{max}-Z(t))$ of the difference value $(Z\text{max}-Z(t))$ from time t1 that is the gradual decrease start time. Then, the processor 35 judges, by the process of step S108, whether the integrated value $\Sigma(Z\text{max}-Z(t))$ from time t1, at which the impedance Z(t) takes the peak value, is greater than the predetermined threshold $\Sigma Z\text{th}$. Here, at time t2, it is judged that the integrated value $\Sigma Z1$, i.e. the integrated value $\Sigma(Z\text{max}-Z(t))$ from time t1 to time t2, is not greater than the predetermined threshold $\Sigma Z\text{th}$. Thus, the output of electric energy from the energy output source 47 is not reduced and is maintained. In addition, at time t2, the notification by the notification device 55 is not executed.

Further, at or immediately after time t3, by the process of step S108, it is judged by the process of step S108 that, for example, the integrated value $\Sigma Z2$, i.e. the integrated value $\Sigma(Z\text{max}-Z(t))$ from time t1 to time t3, is greater than the predetermined threshold $\Sigma Z\text{th}$. Thereby, at or immediately after time t3, the output of electric energy from the energy output source 47 is stopped or reduced by the process of step S109. Besides, at or immediately after time t3, the notification device 55 executes notification, and the surgeon may stop, based on the notification, the output of electric energy from the energy output source 47. Note that the timing of stopping or reducing the output of electric energy from the energy output source 47 is after time t1 that is the gradual decrease start time.

As described above, in the example of FIG. 4, at or immediately near time t1, the entirety of the grasped range of the treated target is divided by cutting. Thus, by the output of electric energy from the energy output source 47 being stopped or reduced at or immediately after time t3, the output of electric energy from the energy output source 47 is stopped or reduced after the time point (t1) at which the entirety of the grasped range of the treated target was divided by cutting. Thereby, it is possible to effectively prevent a part of the grasped range of the treated target from being not divided by cutting and from being left.

In addition, in the example of FIG. 4, at time t3, there occurs substantially no deformation of the pad member 21 due to frictional heat. Thus, in the present embodiment, the output of electric energy from the energy output source 47 is stopped or reduced after the entirety of the grasped range of the treated target was divided by cutting and before the pad member 21 is deformed by frictional heat. Specifically, in the present embodiment, the pad member 21 of the second grasping piece 16 is effectively prevented from being kept in contact with the first grasping piece 15 in the state in which the first grasping piece 15 vibrates with a large amplitude and high vibration velocity, and the abrasion, deformation, etc. of the pad member 21 of the second grasping piece 16 can effectively be prevented.

Here, after the entirety of the grasped range of the treated target is divided by cutting, the degrease amount of the impedance Z per predetermined unit time in the state in which the impedance Z is decreasing from the gradual decrease start time varies in accordance with, for example, the contact state between the pad member 21 and first grasping piece 15. In other words, the impedance Z sharply decreases from the gradual decrease start time or the impedance Z gently decreases from the gradual decrease start time, in accordance with, for example, the contact state between the pad member 21 and first grasping piece 15. In the present embodiment, the output of electric energy is stopped or reduced, based on the integrated value Σ(Zmax−Z(t)) of the difference value (Zmax−Z(t)) from the gradual decrease start time. Thus, it is properly judged whether the gradual decrease start time is the time point at which the entirety of the grasped range of the treated target was divided by cutting, regardless of the degrease amount of the impedance Z per predetermined unit time in the state in which the impedance Z is decreasing from the gradual decrease start time. In short, it is properly judged whether or not the peak of the impedance Z occurs due to the division by cutting. As described above, in the present embodiment, the timing when the treated target is divided by cutting is properly detected. Further, based on the detected proper timing, the output of electric energy from the energy output source 47 is stopped or reduced.

Second Embodiment

Next, a second embodiment of the present invention will be described with reference to FIG. 6 to FIG. 8. In the second embodiment, the configuration of the first embodiment is modified as described below. The same parts as in the first embodiment are denoted by like reference signs, and a description thereof is omitted.

Figure 6:
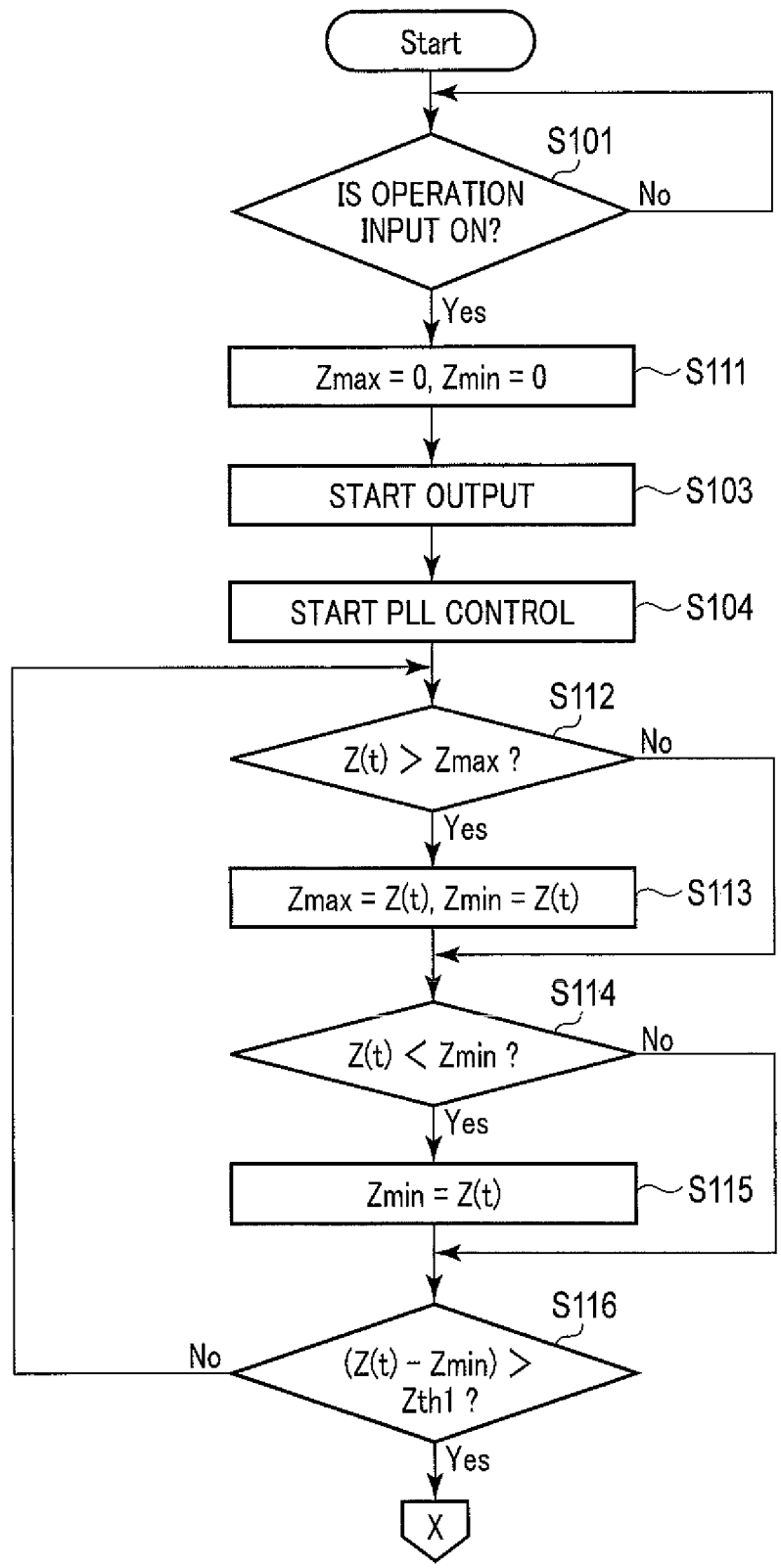
FIG. 6 is a flowchart illustrating a process in a processor of an energy control device according to a second embodiment.
Figure 7:
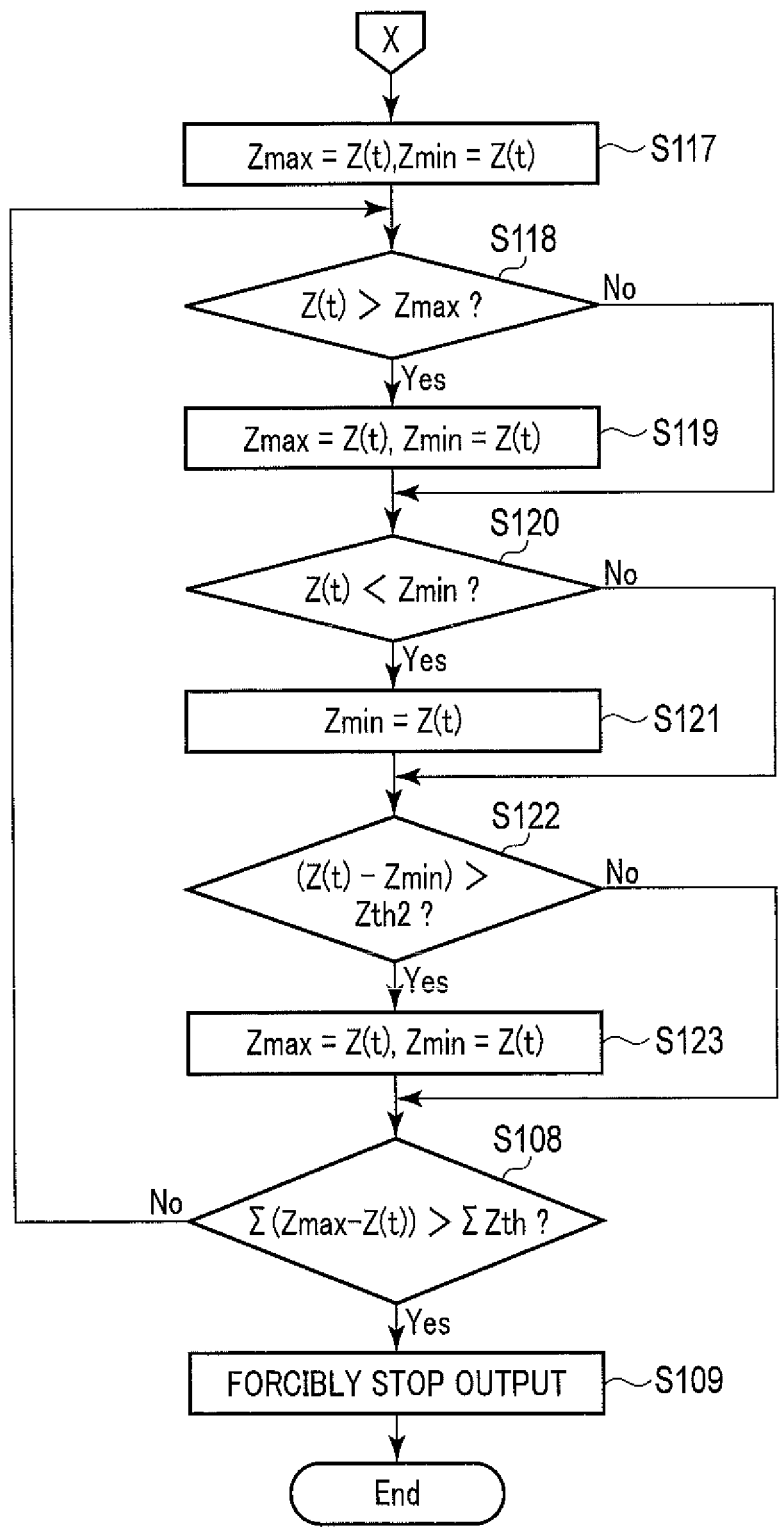
FIG. 7 is a flowchart illustrating a process in the processor of the energy control device according to the second embodiment.

FIG. 6 and FIG. 7 are flowcharts illustrating a process in the processor 35 of the energy control device 3. As illustrated in FIG. 6 and FIG. 7, in the present embodiment, like the first embodiment, if the operation input is executed (step S101—Yes), the processor 35 resets to zero the impedance maximum value Zmax which is a judgment parameter (step S111). Further, in the present embodiment, an impedance minimum value Zmin is used as a judgment parameter, in addition to the impedance maximum value Zmax. The impedance minimum value Zmin is a minimum value of the impedance Z from a certain time point defined by a condition to a time point at which the impedance Z(t) occurs. If the operation input is executed (step S101—Yes), the processor 35 also resets the impedance minimum value Zmin to zero (step S111).

Then, like the first embodiment, the output controller 45 of the processor 35 starts the output of electric energy from the energy output source 47 to the ultrasonic transducer (step S103). After the start of the output of electric energy to the ultrasonic transducer 25, if a predetermined condition is satisfied, the output controller 45 of the processor 35 starts PLL control with respect to the electric energy that is output from the energy output source 47 (step S104). In addition, in this embodiment, like the first embodiment, if the PLL control is started, the characteristic value detector 41 starts detecting the impedance Z, and the output controller 45 controls the output of electric energy from the energy output source 47 by the above-described constant current control which keeps the current value of the output current I constant with time.

In the present embodiment, if the PLL control is started, the gradually decreasing detector 42 of the processor 35 judges whether the impedance Z(t) at time t is greater than the impedance maximum value Zmax that is set (step S112). If the impedance Z(t) is greater than the impedance maximum value Zmax (step S112—Yes), the processor 35 updates the impedance maximum value Zmax to the impedance Z(t) at time t, and updates the impedance minimum value Zmin to the impedance Z(t) (step S113). Then, the process advances to step S114. On the other hand, if the impedance Z(t) is not greater than the impedance maximum value Zmax (step S112—No), the processor 35 holds, without updating, the impedance maximum value Zmax and impedance minimum value Zmin. Then, the process advances to step S114.

Subsequently, the gradually increasing detector 46 of the processor 35 judges, based on the detection result of the impedance Z by the characteristic value detector 41, whether the impedance Z(t) at time t is less than the impedance minimum value Zmin that is set (step S114). If the impedance Z(t) is less than the impedance minimum value Zmin (step S114—Yes), the processor 35 updates the impedance minimum value Zmin to the impedance Z(t) at time t (step S115). Then, the process advances to step S116. On the other hand, if the impedance Z(t) is not less than the impedance minimum value Zmin (step S114-No), the processor 35 holds, without updating, the impedance minimum value Zmin. Then, the process advances to step S116. By the execution of the process of steps S114 and S115, the gradually increasing detector 46 of the processor 35 detects, as the gradual increase start time at which the impedance Z starts a gradual increase after a gradual decrease, the time point when the state in which the impedance Z(t) is less than the impedance minimum value Zmin changed to the state in which the impedance Z(t) is not less than the impedance minimum value Zmin.

Then, the output controller 45 and gradually increasing detector 46 of the processor 35 judge whether a calculation value (Z(t)−Zmin), which is calculated by subtracting the set impedance minimum value Zmin from the impedance Z(t) at time t, is greater than a predetermined threshold Zth1 (step S116). Here, the predetermined threshold Zth1 is a positive value. In addition, the predetermined threshold Zth1 can be set, like the predetermined threshold ΣZth described in the first embodiment. When the calculation value (Z(t)−Zmin) is not greater than the predetermined threshold Zth1 (step S116-No), the process returns to step S112. Then, the processes of step S112 onwards are successively executed. On the other hand, when the calculation value (Z(t)−Zmin) is greater than the predetermined threshold Zth1 (step S116—Yes), the processor 35 updates the impedance maximum value Zmax to the impedance Z(t), and updates the impedance minimum value Zmin to Z(t) (step S117).

If the process of step S117 is executed, the gradually decreasing detector 42 judges whether the impedance Z(t) is greater than the impedance maximum value Zmax that is set (step S118). When the impedance Z(t) is greater than the impedance maximum value Zmax (step S118—Yes), the processor 35 updates the impedance maximum value Zmax to the impedance Z(t) at time t, and updates the impedance minimum value Zmin to the impedance Z(t) (step S119). Then, the process advances to step S120. On the other hand, when the impedance Z(t) is not greater than the impedance maximum value Zmax (step S118—No), the processor 35 holds, without updating, the impedance maximum value Zmax and impedance minimum value Zmin. Then, the process advances to step S120. By the execution of the process of steps S118 and S119, the gradually decreasing detector 42 of the processor 35 detects, as the gradual decrease start time at which the impedance Z starts a gradual decrease after a gradual increase, the time point when the state in which the impedance Z(t) is greater than the impedance maximum value Zmax changed to the state in which the impedance Z(t) is not greater than the impedance maximum value Zmax.

Subsequently, the gradually increasing detector 46 of the processor 35 judges whether the impedance Z(t) at time t is less than the impedance minimum value Zmin that is set (step S120). If the impedance Z(t) is less than the impedance minimum value Zmin (step S120—Yes), the processor 35 updates the impedance minimum value Zmin to the impedance Z(t) at time t (step S121). Then, the process advances to step S122. On the other hand, if the impedance Z(t) is not less than the impedance minimum value Zmin (step S120—No), the processor 35 holds, without updating, the impedance minimum value Zmin. Then, the process advances to step S122. By the execution of the process of steps S120 and S121, the gradually increasing detector 46 of the processor 35 detects, as the gradual increase start time at which the impedance Z starts a gradual increase after a gradual decrease, the time point when the state in which the impedance Z(t) is less than the impedance minimum value Zmin changed to the state in which the impedance Z(t) is not less than the impedance minimum value Zmin.

Then, the output controller 45 and gradually increasing detector 46 of the processor 35 judge whether a calculation value (Z(t)−Zmin), which is calculated by subtracting the set impedance minimum value Zmin from the impedance Z(t) at time t, is greater than a predetermined threshold Zth2 (step S122). Here, the predetermined threshold Zth2 is a positive value. The predetermined threshold Zth2 may have the same value as the predetermined threshold Zth1, or may have a different value from the predetermined threshold Zth1. In addition, the predetermined threshold Zth2 can be set, like the predetermined threshold ΣZth described in the first embodiment. When the calculation value (Z(t)−Zmin) is greater than the predetermined threshold Zth2 (step S122—Yes), the processor 35 updates the impedance maximum value Zmax to the impedance Z(t), and updates the impedance minimum value Zmin to Z(t) (step S123). Then, the process advances to step S108. On the other hand, when the calculation value (Z(t)−Zmin) is not greater than the predetermined threshold Zth2 (step S122-No), the processor 35 holds, without updating, the impedance maximum value Zmax and impedance minimum value Zmin. Then, the process advances to step S108.

Then, as in the process at or after the gradual decrease start time in the first embodiment, the calculator 43 calculates the difference value (Zmax−Z(t)) which is obtained by subtracting the impedance Z(t) from the peak value of the impedance Z(t) at the gradual decrease start time, which is the impedance maximum value Zmax. In addition, the processor 35 judges whether the integrated value Σ(Zmax−Z(t)) of the difference value (Zmax−Z(t)) from the gradual decrease start time to the time t is greater than the predetermined threshold ΣZth (step S108). When it is judged that the integrated value Σ(Zmax−Z(t)) is greater than the predetermined threshold ΣZth (step S108—Yes), the output controller 45 of the processor 35 forcibly stops the output of electric energy from the energy output source 47 to the ultrasonic transducer 25 (step S109), like the first embodiment. At this time, like the first embodiment, the output of electric energy from the energy output source 47 to the ultrasonic transducer 25 may be reduced, or the notification by the notification device 55 may be executed. Besides, the stop or reduction of the output of electric energy, and the notification by the notification device 55 may be combined. On the other hand, when it is judged that the integrated value Σ(Zmax−Z(t)) is not greater than the predetermined threshold ΣZth (step S108—No), the process returns to step S118. Then, the processes of step S118 onwards are successively executed.

Figure 8:
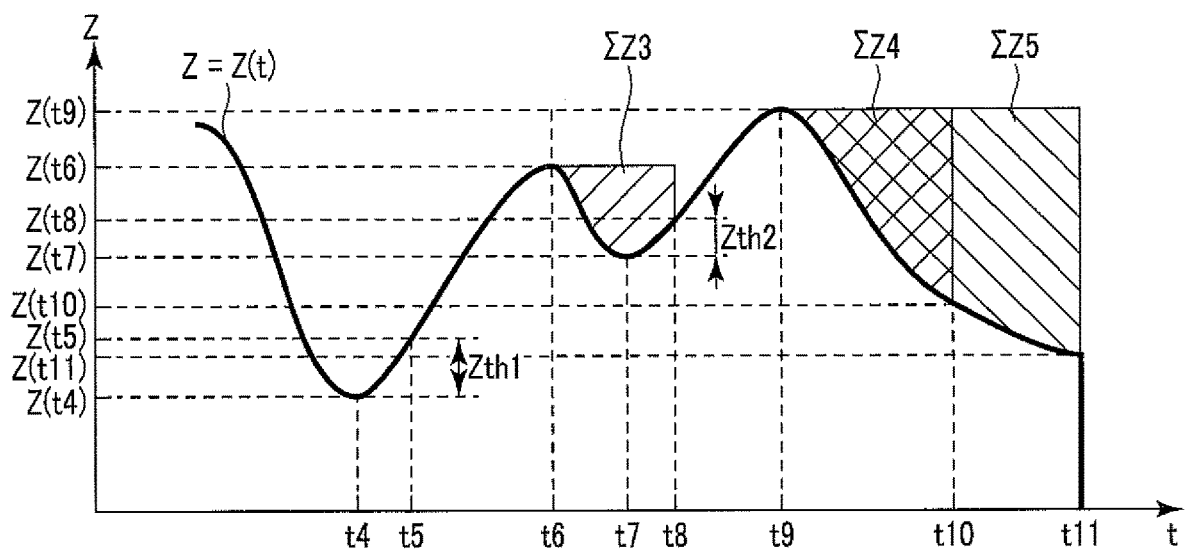
FIG. 8 is a schematic view illustrating an example of a variation with time of an impedance of the ultrasonic transducer in a state in which a grasped treated target is cut and opened, while being coagulated, by ultrasonic vibration, the example of FIG. 8 being different from the example of FIG. 4.

FIG. 8 is a view illustrating an example of a variation with time of the impedance Z of the ultrasonic transducer 25 in the state in which the grasped treated target is cut and opened, while being coagulated, by ultrasonic vibration, the example of FIG. 8 being different from the example of FIG. 4. Also in FIG. 8, the ordinate axis indicates the impedance Z, and the abscissa axis indicates time t. Here, as described above, if the PLL control is started, the frequency in the output of electric energy is adjusted in such a state that the phase difference between the output current I and output voltage V becomes lower than a predetermined threshold value. Thus, during a certain period from the start time of the PLL control, there is a case in which the impedance Z gradually decreases. In this case, after the impedance Z gradually decreases during the period from the start time of the PLL control, the impedance Z gradually increases. In the example of FIG. 8, the impedance Z gradually decreases until time t4 from the start time of the PLL control. During a certain period from time t4, the impedance Z gradually increases.

In the present embodiment, the process illustrated in FIG. 6 and FIG. 7 is executed. Thus, if the impedance Z varies with time, as illustrated in FIG. 8, each of the impedance maximum value Zmax and impedance minimum Zmin is updated to the impedance Z(t) by the processes of steps S112 and S113 at or immediately after the start time of the PLL control. In addition, until time t4, by the processes of steps S114 and S115, the impedance minimum value Zmin is continuously updated to the impedance Z(t). Thus, the calculation value (Z(t)−Zmin) has a negative value until time t4, and it is judged by the process of step S116 that the calculation value (Z(t)−Zmin) is not greater than the predetermined threshold Zth1. Accordingly, until time t4, the process does not advance to step S117, and the process of step S108 of judging whether the integrated value Σ(Zmax−Z(t)) is greater than the predetermined threshold ΣZth is not executed.

In the example of FIG. 8, the impedance Z gradually increases for a certain period from time t4, and, at time t5, the impedance Z(t5) has a value at which the impedance Z(t4) at time t4 has increased by the predetermined threshold Zth1. Then, during a certain period from time t5, the impedance Z gradually increases. In the present embodiment, since the process illustrated in FIG. 6 and FIG. 7 is executed, the impedance Z(t4) at time t4 is held as the impedance minimum value Zmin by the process of step S114 while the impedance Z is gradually increasing from time t4. In addition, until time t5, it is judged that the calculation value (Z(t)−Zmin) is not greater than the predetermined threshold Zth1. Accordingly, until time t5, the process does not advance to step S117. At or immediately after time t5, the processor 35 judges that the calculation value (Z(t)−Zmin) is greater than the predetermined threshold Zth1, and the process advances to step S117. In addition, at or immediately after time t5, by the process of step S117, each of the impedance maximum value Zmax and impedance minimum value Zmin is updated to the impedance Z(t).

As described above, in the present embodiment, even in the case in which the impedance Z gradually increases after gradually decreasing for a certain period from the start time of the PLL control, the process does not advance to step S117 until the increase amount of the impedance Z from the gradual increase start time becomes greater than the predetermined threshold Zth1. Specifically, the process of step S108 of judging whether the integrated value $\Sigma(Zmax-Z(t))$ is greater than the predetermined threshold $\Sigma Zth$ is not executed until the impedance Z increases by a certain increase amount from the gradual increase start time. Accordingly, while the ultrasonic impedance Z is gradually decreasing from the start time of the PLL control, the output of electric energy from the energy output source 47 is neither stopped nor reduced.

Besides, when the thickness of the grasped treated target is large or when the degree of wetting of the treated target is large, there may be a case in which a peak of the impedance Z occurs at an instant when the contact surface of the treated target with the grasping piece 15 or 16 has begun to be cut. In this case, the peak of the impedance Z occurs due to the beginning of the cutting of the contact surface of the treated target, before the occurrence of the above-described peak due to the division by cutting. In the example illustrated in FIG. 8, the peak of the impedance Z due to the division by cutting occurs at time t9, and the peak of the impedance also occurs at time t6 prior to time t9. In addition, the impedance Z gradually decreases from time t6 to time t7, and the impedance Z gradually increases from time t7 to time t9.

In the present embodiment, the process illustrated in FIG. 6 and FIG. 7 is executed. Thus, in the example illustrated in FIG. 8, until time t6 after time t5, by the processes of steps S118 and S119, the impedance maximum value Zmax is continuously updated to the impedance Z(t). In addition, until time t6, it is judged in step S120 that the impedance Z(t) is not less than the impedance minimum value Zmin, and it is judged in step S122 that the calculation value (Z(t)−Zmin) is not greater than the predetermined threshold Zth2. Since the impedance maximum value Zmax is continuously updated to the impedance Z(t), the integrated value $\Sigma(Zmax-Z(t))$ of the difference value (Zmax−Z(t)), which is obtained by subtracting the impedance Z(t) from the impedance maximum value Zmax, is continually reset to zero until time t6. Accordingly, until time t6, by the process of step S108, it is judged that the integrated value $\Sigma(Zmax-Z(t))$ is not greater than the predetermined threshold $\Sigma Zth$. Thus, until time t6, the process of step S109 is not executed, and the output of electric energy from the energy output source 47 is maintained without being reduced.

Further, immediately after time t6, the gradually decreasing detector 42 judges, by the process of step S118, that the impedance Z(t) is not greater than the impedance Z(t6) that is the impedance maximum value Zmax. Thereby, the gradually decreasing detector 42 detects time t6 as the gradual decrease start time of the impedance Z. In addition, the impedance Z(t6) at time t6 is set as the peak value of the impedance Z(t).

In addition, in the example of FIG. 8, the impedance Z gradually increases for a certain period from time t7, and, at time t8, the impedance Z(t8) has a value at which the impedance Z(t7) at time t7 has increased by the predetermined threshold Zth2. Then, during a certain period from time t8, the impedance Z gradually increases. Here, the integrated value $\Sigma(Zmax-Z(t))$ from time t6 that is the gradual decrease start time to time t8 is defined as an integrated value $\Sigma Z3$. In the example of FIG. 8, the integrated value $\Sigma Z3$ is equal to or less than the predetermined threshold $\Sigma Zth$. In addition, in the example of FIG. 8, an area of a part surrounded by a straight line t=t8, a straight line Z=Z(t6) and a curve line Z=Z(t) becomes the integrated value $\Sigma Z3$ of the difference value (Zmax−Z(t)) from time t6 to time t8.

In the present embodiment, the process illustrated in FIG. 6 and FIG. 7 is executed. Thus, until time t7 after time t6, by the processes of steps S120 and S121, the impedance minimum value Zmin is continuously updated to the impedance Z(t). Then, while the impedance Z is gradually increasing from time t7, by the process of step S120, the impedance Z(t7) at time t7 is held as the impedance minimum value Zmin. In addition, until time t8, it is judged that the calculation value (Z(t)−Zmin) is not greater than the predetermined threshold Zth2. As described above, the integrated value $\Sigma Z3$ of the difference value (Zmax−Z(t)) from time t6 to time t8 is equal to or less than the predetermined threshold $\Sigma Zth$. Thus, until time t8, by the process of step S108, it is judged that the integrated value $\Sigma(Zmax-Z(t))$ of the difference value (Zmax−Z(t)) from time t6 that is the gradual decrease start time is less than the predetermined threshold $\Sigma Zth$. Accordingly, until time t8, the process of step S109 is not executed.

Then, at or immediately after time t8, the processor 35 judges that the calculation value (Z(t)−Zmin) is greater than the predetermined threshold Zth2. In addition, at or immediately after time t8, by the process of step S123, each of the impedance maximum value Zmax and impedance minimum value Zmin is updated to the impedance Z(t). Since the impedance maximum value Zmax is updated, the integrated value $\Sigma(Zmax-Z(t))$ of the difference value (Zmax−Z(t)), which is obtained by subtracting the impedance Z(t) from the impedance maximum value Zmax, is reset to zero. Accordingly, at or immediately after time t8, by the process of step S108, it is judged that the integrated value $\Sigma(Zmax-Z(t))$ is not greater than the predetermined threshold $\Sigma Zth$.

Further, between time t8 and time t9, by the processes of steps S118 and S119, the impedance maximum value Zmax is continuously updated to the impedance Z(t). In addition, until time t9, it is judged in step S120 that the impedance Z(t) is not less than the impedance minimum value Zmin, and it is judged in step S122 that the calculation value (Z(t)−Zmin) is not greater than the predetermined threshold Zth2. Since the impedance maximum value Zmax is continuously updated to the impedance Z(t), the integrated value $\Sigma(Zmax-Z(t))$ of the difference value (Zmax−Z(t)), which is obtained by subtracting the impedance Z(t) from the impedance maximum value Zmax, is continuously reset to zero from time t8 to time t9. Accordingly, until time t9, by the process of step S108, it is judged that the integrated value $\Sigma(Zmax-Z(t))$ is not greater than the predetermined threshold $\Sigma Zth$. Thus, until time t9, the process of step S109 is not executed, and the output of electric energy from the energy output source 47 is not reduced and is maintained.

As described above, in the present embodiment, before the integrated value $\Sigma(Zmax-Z(t))$ of the difference value (Zmax−Z(t)) from the gradual decrease start time becomes greater than the predetermined threshold $\Sigma Zth$, if the gradual increase start time of the impedance Z is detected and the increase amount of the impedance Z from the gradual increase start time becomes greater than the predetermined increase amount (Zth2), the processor 35 resets to zero the integrated value $\Sigma(Zmax-Z(t))$ of the difference value (Zmax−Z(t)) from the gradual decrease start time. Specifically, in the present embodiment, even when another peak occurs before the peak of the impedance Z due to the division by cutting, if the impedance Z gradually increases by a greater increase amount than the predetermined threshold Zth2 before the integrated value $\Sigma(Zmax-Z(t))$ from the gradual decrease start time (e.g. t6) becomes greater than the predetermined threshold $\Sigma Zth$, it is continuously judged by the process of step S108 that the integrated value $\Sigma(Zmax-Z(t))$ of the difference value (Zmax−Z(t)) from the gradual decrease start time is not greater than the predetermined threshold $\Sigma Zth$. Accordingly, before the time of occurrence of the peak of the impedance Z due to the division by cutting, the output of the electric energy from the energy output source 47 is effectively prevented from being stopped or reduced due to another peak.

In addition, in the example of FIG. 8, at or after time t9, the impedance Z gradually decreases once again. Here, in the example of FIG. 8, time t10 after time t9, and time t11 after time t10 are defined. Further, the integrated value $\Sigma(Zmax-Z(t))$ from time t9 that is the gradual decrease start time to time t10 is defined as $\Sigma Z4$, and the integrated value $\Sigma(Zmax-Z(t))$ from time t9 to time t11 is defined as $\Sigma Z5$. In the example of FIG. 8, the integrated value $\Sigma Z4$ is not greater than the predetermined threshold $\Sigma Zth$, and the integrated value $\Sigma Z5$ is greater than the predetermined threshold $\Sigma Zth$. Besides, the integrated value $\Sigma(Zmax-Z(t))$ of the difference value (Zmax−Z(t)) from time t9 that is the gradual decrease start time changes, at time t11, from the state in which the integrated value $\Sigma(Zmax-Z(t))$ is not greater than the predetermined threshold $\Sigma Zth$ to the state in which the integrated value E (Zmax−Z(t)) is greater than the predetermined threshold $\Sigma Zth$. In addition, in the example of FIG. 8, at or immediately near time t9, the entirety of the grasped range of the treated target is divided by cutting, and, at time t11, there occurs substantially no deformation of the pad member 21 due to frictional heat. Note that, in the example of FIG. 8, an area of a part surrounded by a straight line t=t10, a straight line Z=Z(t9) and a curve line Z=Z(t) becomes the integrated value $\Sigma Z4$ of the difference value (Zmax−Z(t)) from time t9 to time t10. In addition, an area of a part surrounded by a straight line t=t11, straight line Z=Z(t9) and curve line Z=Z(t) becomes the integrated value $\Sigma Z5$ of the difference value (Zmax−Z(t)) from time t9 to time t11.

In the present embodiment, the process of FIG. 6 and FIG. 7 is executed. Thus, in the example of FIG. 8, immediately after time t9, the gradually decreasing detector 42 judges, by the process of step S118, that the impedance Z(t) is not greater than the impedance Z(t9) that is the impedance maximum value Zmax. Thereby, the gradually decreasing detector 42 updates the gradual decrease start time of the impedance Z to time t9. Specifically, the gradually decreasing detector 42 updates the gradual decrease start time to the time point at which the gradual decrease is started once again, based on the fact that the impedance Z started the gradual decrease once again after the increase amount of the impedance Z from the gradual increase start time become greater than the predetermined increase amount (Zth2). In addition, the peak value of the impedance Z(t) is updated to the impedance Z(t9) at time t9 that is the updated gradual decrease start time.

Then, from time t9, the same process as the process after time t1 in the example of FIG. 4 is executed. Accordingly, in the example of FIG. 8, the difference value (Zmax−Z(t)), which is obtained by subtracting the impedance Z(t) from the impedance Z(t9) that is the updated peak value, is calculated, and the integrated value $\Sigma(Zmax-Z(t))$ of the difference value (Zmax−Z(t)) from time t9, which is the updated gradual decrease start time, is calculated. Then, the processor 35 judges, by the process of step S108, whether the integrated value $\Sigma(Zmax-Z(t))$ from time t9, at which the impedance Z(t) takes the peak value, is greater than the predetermined threshold $\Sigma Zth$. Here, at time t10, it is judged that the integrated value $\Sigma Z4$, i.e. the integrated value $\Sigma(Zmax-Z(t))$ from time t9 to time t10, is not greater than the predetermined threshold $\Sigma Zth$. Thus, the output of electric energy from the energy output source 47 is not reduced and is maintained. In addition, at time t10, the notification by the notification device 55 is not executed.

In addition, at or immediately after time t11, by the process of step S108, it is judged that, for example, the integrated value $\Sigma Z5$, i.e. the integrated value $\Sigma(Zmax-Z(t))$ from time t9 to time t11, is greater than the predetermined threshold $\Sigma Zth$. Thereby, at or immediately after time t11, by the process of step S109, the output of electric energy from the energy output source 47 is stopped or reduced. Besides, at or immediately after time t11, the notification device 55 may execute notification.

In the example of FIG. 8, as described above, at time t11, there occurs substantially no deformation of the pad member 21 due to frictional heat. Thus, since the output of electric energy from the energy output source 47 is stopped or reduced at or immediately after time t11, the output of electric energy from the energy output source 47 is stopped or reduced after the entirety of the grasped range of the treated target was divided by cutting and before the pad member 21 is deformed by frictional heat.

As described above, in the present embodiment, the timing at which the treated target is divided by cutting can properly be detected in each of the case in which the impedance Z gradually decreased for a certain period from the start time of the PLL control and then gradually increased, and the case in which, before the peak of the impedance Z occurs due to the division by cutting, another peak occurred. In addition, based on the detected properly timing, the output of electric energy from the energy output source 47 is stopped or reduced.

(Modifications)

Figure 9:
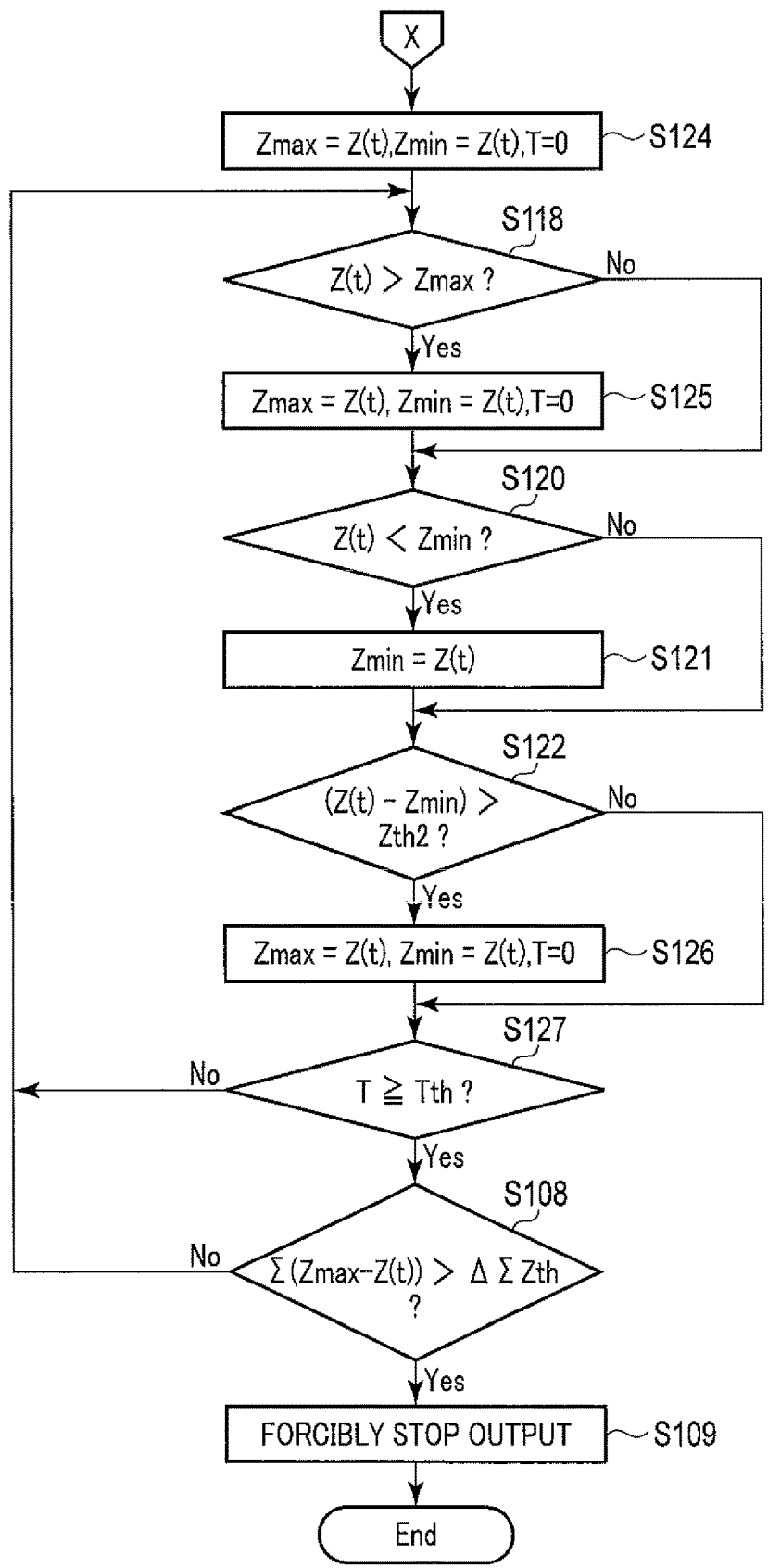
FIG. 9 is a flowchart illustrating a part of a process in the processor of the energy control device according to one modification of the second embodiment.

In one modification of the second embodiment, which is illustrated in FIG. 9, a count time T is used as a judgment parameter, in addition to the impedance maximum value Zmax and impedance minimum value Zmin. The count time T is an elapsed time from a certain time point defined by a condition to a time point at which the impedance Z(t) occurs. The count time T is set, for example, based on a variation with time of the impedance Z. In the present modification, like the second embodiment, the processes of steps S101, S111, S103, S104, and S112 to S116 are executed.

In the present modification, in step S116, if it is judged that the calculation value (Z(t)−Zmin) is greater than the predetermined threshold Zth1 (step S116—Yes), the processor 35 updates each of the impedance maximum value Zmax and the impedance minimum value Zmin to Z(t), and resets the count time T to zero (step S124). Then, like the second embodiment, the gradually decreasing detector 42 judges whether the impedance Z(t) is greater than the impedance maximum value Zmax that is set (step S118). When the impedance Z(t) is greater than the impedance maximum value Zmax (step S118—Yes), the processor 35 updates each of the impedance maximum value Zmax and the impedance minimum value Zmin to the impedance Z(t), and resets the count time T to zero (step S125). Then, the process advances to step S120. On the other hand, when the impedance Z(t) is not greater than the impedance maximum value Zmax (step S118—No), the processor 35 holds, without updating, the impedance maximum value Zmax and impedance minimum value Zmin, and does not reset the count time T. Then, the process advances to step S120.

In the present modification, like the second embodiment, the processes of steps S120 and S121 are executed, and the processor 35 judges in step S122 whether the calculation value (Z(t)−Zmin) is greater than the predetermined threshold Zth2 (step S122). In this modification, when the calculation value (Z(t)−Zmin) is greater than the predetermined threshold Zth2 (step S122—Yes), the processor 35 updates each of the impedance maximum value Zmax and the impedance minimum value Zmin to Z(t), and resets the count time T to zero (step S126). Then, the process advances to step S127. On the other hand, when the calculation value (Z(t)−Zmin) is not greater than the predetermined threshold Zth2 (step S122—No), the processor 35 holds, without updating, the impedance maximum value Zmax and impedance minimum value Zmin, and does not reset the count time T. Then, the process advances to step S127.

In the present modification, the output controller 45 of the processor 35 judges whether the count time T is equal to or greater than a predetermined time Tth (step S127). When the count time T is less than the predetermined time Tth (step S127—No), the process returns to step S118. Further, the processes of step S118 onwards are successively executed. On the other hand, when the count time T is equal to or greater than the predetermined time Tth (step S127—Yes), the process advances to step S108. Then, like the second embodiment, the processes of steps S108 and S109 are executed. Note that the predetermined time Tth can be set, like the above-described predetermined threshold ΣZth.

In the present modification, by the above-described process being executed, the process of the processor 35 does not advance to step S108 before the predetermined time Tth has passed since the gradual decrease start time. Specifically, after the passage of the predetermined time Tth from the gradual decrease start time, the process of step S108 is executed to judge whether the integrated value Σ(Zmax−Z(t)) of the difference value (Zmax−Z(t)) from the gradual decrease start time is greater than the predetermined threshold ΣZth. After the passage of the predetermined time Tth from the gradual decrease start time, if it is judged that the integrated value Zmax−Z(t)) is greater than the predetermined threshold ΣZth, the output controller 45 stops or reduces the output energy from the energy output source 47, or causes the notification device 55 to execute notification.

In another modification, the process of steps S112 to S116 in FIG. 6 and FIG. 7 is not executed. Instead, a process based on a count time T', which is different from the count time T, is executed. In this case, the count time T' is zero at the time of the start of the PLL control, and indicates the elapsed time from the start time of the PLL control. In this modification, if the PLL control is started in step S104, the processor 35 judges whether the count time T' is equal to or greater than a predetermined time T'th. Then, the process advances to step S117, only when the count time T' is equal to or greater than the predetermined time T'th. Thereby, the process of step S108 of judging whether the integrated value Σ(Zmax−Z(t)) is greater than the predetermined threshold ΣZth is not executed until the predetermined time T'th has passed since the start time of the PLL control. Accordingly, in the present modification, like the second embodiment, while the ultrasonic impedance Z is gradually decreasing from the start time of the PLL control, the output of electric energy from the energy output source 47 is neither stopped nor reduced.

Note that the predetermined time T'th can be set, like the above-described predetermined threshold ΣZth.

Additionally, in one modification, the state in which the processor 35 executes the process of step S108 of judging whether the integrated value Σ(Zmax−Z(t)) of the difference value (Zmax−Z(t)) from the gradual decrease start time is greater than the predetermined threshold ΣZth and the state in which the processor 35 does not execute the process of step S108 are switched by the surgeon's operation. In this case, the energy control device 3 is provided with an input device (not shown) such as a touch panel, and a user interface (not shown). Based on the operation through the input device, switching is made as to whether the processor 35 executes the judgment, the judgement being related to whether the integrated value Σ(Zmax−Z(t)) is greater than the predetermined threshold ΣZth. Note that in the state in which the processor 35 does not execute the judgment of step S108, the output of electric energy from the energy output source 47 is neither stopped nor reduced, based on the integrated value Σ(Zmax−Z(t)).

Additionally, in one modification, one of the output voltage V and output electric power P from the energy output source 47 to the ultrasonic transducer 25 may be used as the electric characteristic value of the electric energy that is output from the energy output source 47, in place of the impedance Z or in addition to the impedance Z. As described above, in the state in which the electric energy is being supplied from the energy output source 47 to the ultrasonic transducer 25, the output of electric energy from the energy output source 47 is controlled by the constant current control which keeps the current value of the output current I constant with time. In addition, in the constant current control, the output voltage V and output electric power P are adjusted in accordance with the variation of the impedance Z. Thus, from the start time of the PLL control, the variation with time of each of the output voltage V and output electric power P exhibits the same tendency as the variation with time of the impedance Z. Accordingly, even when the process illustrated in FIG. 5, the process illustrated in FIG. 6 and FIG. 7 and the process illustrated in FIG. 9 are executed by using one of the output voltage V and output electric power P in place of the impedance Z, the same function and advantageous effects as in the above-described embodiments, etc. can be obtained. In this case, either a voltage maximum value Vmax of the output voltage V or a power maximum value Pmax of the output electric power P is used in place of the impedance maximum value Zmax. Besides, one of a difference value (Vmax−V(t)) and a difference value (Pmax−P(t)) is used in place of the difference value (Zmax−Z(t)), and one of an integrated value E(Vmax−V(t)) and an integrated value E(Pmax P(t)) is used in place of the integrated value Σ(Zmax−Z(t)). Further, a predetermined threshold ΣVth and a predetermined threshold ΣPth are used in place of the predetermined threshold ΣZth.

Additionally, in one modification, in addition to outputting electric energy to the ultrasonic transducer 25, the energy output source 47 may output electric energy to the ultrasonic treatment instrument 2, this electric energy being different from the electric energy which is supplied to the ultrasonic transducer 25. In this case, for example, high-frequency electric power is supplied as electric energy from the energy output source 47 to the first grasping piece 15 and the holder member 22 of the second grasping piece 16. Thereby, a high-frequency electric current flows between the first grasping piece 15 and the holder member 22 through the grasped treated target. By the heat generated by the high-frequency current, the treated target is denatured, and coagulation is promoted.

In the energy control device (3) of the above-described embodiments, etc., the gradually decreasing detector (42) detects the gradual decrease start time at which the electric characteristic value (Z; V; P) starts a gradual decrease after a gradual increase, based on the detection result of the electric characteristic value (Z; V; P) in relation to the electric energy which is output from the energy output source (47) to the ultrasonic transducer (25). The calculator (43) calculates the integrated value NE (Zmax−Z(t)); Σ(Vmax−V(t)); E(Pmax−P(t))) from the gradual decrease start time of the difference value (Zmax−Z(t); Vmax−V(t); Pmax−P(t)) which is obtained by subtracting the electric characteristic value (Z; V; P) from the peak value (Zmax; Vmax; Pmax) that is the electric characteristic value (Z; V; P) at the gradual decrease start time. Based on a fact that the integrated value ((Σ(Zmax−Z(t)); Σ(Vmax−V(t)); E(Pmax−P(t))) become greater than the predetermined threshold (ΣZth; ΣVth; Pth) after the gradual decrease start time, the controller (45) executes at least one of causing the energy output source (47) to stop or reduce the output of the electric energy to the ultrasonic transducer (25), and notifying that the integrated value HE(Zmax−Z(t)); Σ(Vmax−V(t)); E(Pmax−P(t))) become greater than the predetermined threshold (ΣZth; ΣVth; ΣPth).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An energy control device for use in combination with an ultrasonic treatment instrument, the ultrasonic treatment instrument including an ultrasonic transducer configured to generate ultrasonic vibration by being supplied with electric energy, and an end effector configured to perform a treatment by using the ultrasonic vibration generated by the ultrasonic transducer, the energy control device comprising:
   an energy output source configured to output the electric energy to the ultrasonic transducer; and
   a processor configured to:
      detect an electric characteristic value in relation to the electric energy which is output to the ultrasonic transducer;
      detect, based on a detection result of the electric characteristic value, a decrease start time at which the electric characteristic value starts a decrease after the electric characteristic value increases;
      calculate, with the electric characteristic value at the decrease start time being set as a peak value, an integrated value of a difference value from the decrease start time, the difference value being obtained by subtracting the electric characteristic value from the peak value;
      execute, based on a fact that the integrated value become greater than a predetermined threshold after the decrease start time, at least one of causing the energy output source to stop or reduce the output of the electric energy to the ultrasonic transducer, and notifying that the integrated value become greater than the predetermined threshold;
      set an increase start time at which the electric characteristic value starts an increase;
      calculate an increase amount of the electric characteristic value from the increase start time; and
      reset to zero the integrated value of the difference value from the decrease start time, in a case in which, before the integrated value from the decrease start time becomes greater than the predetermined threshold, the gradual increase start time was detected and the increase amount of the electric characteristic value from the increase start time become greater than a predetermined increase amount.

2. The energy control device of claim 1, wherein
based on a fact that the electric characteristic value started the decrease once again after the increase amount of the electric characteristic value from the increase start time become greater than the predetermined increase amount, the processor is configured to update the decrease start time to a time point at which the electric characteristic value started the decrease once again, and configured to update the peak value to the electric characteristic value at the updated decrease start time,
the processor is configured to calculate an integrated value of a difference value from the updated decrease start time, the difference value being obtained by subtracting the electric characteristic value from the updated peak value, and
the processor is configured to execute, based on a fact that the integrated value of the difference value become greater than the predetermined threshold after the updated decrease start time, at least one of causing the energy output source to stop or reduce the output of the electric energy to the ultrasonic transducer, and notifying that the integrated value become greater than the predetermined threshold.

3. The energy control device of claim 1, wherein
the processor is configured to judge whether the integrated value of the difference value is greater than the predetermined threshold after a predetermined time has passed since the decrease start time, and configured to execute, when the controller judged that the integrated value is greater than the predetermined threshold, at least one of causing the energy output source to stop or reduce the output of the electric energy, and notifying that the integrated value become greater than the predetermined threshold.

4. The energy control device of claim 1, wherein
the processor is configured to detect, as the electric characteristic value, at least one of an impedance of the ultrasonic transducer, an output voltage from the energy output source to the ultrasonic transducer, and an output electric power from the energy output source to the ultrasonic transducer.

5. A treatment system comprising:
the energy control device of claim 1; and
the ultrasonic treatment instrument including the ultrasonic transducer and the end effector.

6. The treatment system of claim 5, wherein
the end effector includes a first grasping piece to which the ultrasonic vibration is transmitted, and a second grasping piece which is openable and closable relative to the first grasping piece, and
the second grasping piece includes a pad member configured to be abuttable on the first grasping piece in a state in which the first grasping piece and the second grasping piece are closed.

7. The treatment system of claim 5, wherein
the ultrasonic treatment instrument includes a storage medium in which the predetermined threshold is stored, and
the processor is configured to read the predetermined threshold from the storage medium by the ultrasonic treatment instrument being connected to the energy control device.

8. The treatment system of claim 5, wherein
the ultrasonic treatment instrument includes a storage medium in which identification information is stored, and
the processor is configured to read the identification information from the storage medium by the ultrasonic treatment instrument being connected to the energy control device, and configured to set the predetermined threshold, based on the read identification information.

9. An actuating method of an energy control device, the energy control device being used in combination with an ultrasonic treatment instrument, the ultrasonic treatment instrument including an ultrasonic transducer configured to generate ultrasonic vibration by being supplied with electric energy, and an end effector configured to perform a treatment by using the ultrasonic vibration generated by the ultrasonic transducer, the actuating method comprising:
   outputting the electric energy to the ultrasonic transducer;
   detecting an electric characteristic value in relation to the electric energy which is output to the ultrasonic transducer;
   detecting, based on a detection result of the electric characteristic value, a decrease start time at which the electric characteristic value starts a decrease after the electric characteristic value increases;
   calculating, with the electric characteristic value at the decrease start time being set as a peak value, an integrated value of a difference value from the decrease start time, the difference value being obtained by subtracting the electric characteristic value from the peak value;
   executing, based on a fact that the integrated value become greater than a predetermined threshold after the decrease start time, at least one of stopping or reducing the output of the electric energy to the ultrasonic transducer, and notifying that the integrated value become greater than the predetermined threshold;
   setting an increase start time at which the electric characteristic value starts an increase;
   calculating an increase amount of the electric characteristic value from the increase start time; and
   resetting to zero the integrated value of the difference value from the decrease start time, in a case in which, before the integrated value from the decrease start time becomes greater than the predetermined threshold, the gradual increase start time was detected and the increase amount of the electric characteristic value from the increase start time become greater than a predetermined increase amount.

* * * * *